United States Patent [19]

Chakravarty et al.

[11] Patent Number: 5,668,279

[45] Date of Patent: Sep. 16, 1997

[54] SUBSTITUTED PHTHALAZINONES AS NEUROTENSIN ANTAGONISTS

[75] Inventors: Prasun K. Chakravarty, Edison; Elizabeth M. Naylor, Scotch Plains; Anna Chen, Rahway, all of N.J.

[73] Assignee: Merck & Co., Inc., Rahway, N.J.

[21] Appl. No.: 411,655

[22] PCT Filed: Oct. 28, 1993

[86] PCT No.: PCT/US93/10386

§ 371 Date: Apr. 6, 1995

§ 102(e) Date: Apr. 6, 1995

[87] PCT Pub. No.: WO94/10151

PCT Pub. Date: May 11, 1994

Related U.S. Application Data

[63] Continuation of Ser. No. 970,358, Nov. 2, 1992, abandoned.

[51] Int. Cl.$^6$ ............ C07D 237/32; C07D 401/04; C07D 409/04; C07D 413/10

[52] U.S. Cl. ............ 544/119; 544/62; 544/232; 544/237

[58] Field of Search ............ 544/232, 237, 544/119, 62; 514/80, 222.2, 226.8, 228.2, 234.5, 248

[56] References Cited

U.S. PATENT DOCUMENTS

| | | | |
|---|---|---|---|
| 4,393,062 | 7/1983 | Brittain et al. | 544/237 |
| 4,425,269 | 1/1984 | Christy et al. | 260/112.5 |
| 4,439,359 | 3/1984 | Holly et al. | 260/112.5 |
| 5,204,354 | 4/1993 | Chakravarty et al. | 544/283 |
| 5,250,558 | 10/1993 | Chakravarty et al. | 514/383 |

FOREIGN PATENT DOCUMENTS 477049  8/1991  European Pat. Off. .

OTHER PUBLICATIONS

Gully et al, *Proc. Nat. Acad. Sci.* 90, pp. 65–69 (1993).
Snider et al, *Bioorganic & Medicinal Chemistry Letters*, 2 (12) pp. 1535–1540 (1992).
Elliott et al, *Proc. Nat. Acad. Sci.* 90, pp. 219–245 (1993).
Brouard et al, *European Journal of Pharmacology*, 253, pp. 289–291 (1994).
de Quidt, M. and Emson, P. *Brain Research*, 274: pp. 376–380 (1983).
Levant B. and Nemcroff, C.B. *Cur. Top. in Neuro.*, 8: pp. 232–262 (1988).
Rompre, P. et al. *Eur. J. of Pharm.* 211: pp. 295–303 (1992).
Stoessl, A. and Szczutkowski, E. *Brain Research*, 558: pp. 289–295 (1991).
Prange, A.J. Jr. and Nemeroff, C. B. *Annals NY Acad. of Sciences*, pp. 368–375 (1982).
Szigethy, E and Beaudet, A. *J. of Comp. Neurology*, 279: pp. 128–137 (1989).

Blaha, C.D. et al., *Neroscience*, 34: No. 3. pp. 699–705 (1990).
Glimcher, P.W. et al., *Brain Research*, 403: pp. 147–150 (1987).
Kitabgi, P. *Neurochem. Int.*, 14: No. 2, pp. 111–119 (1989).
Shi, W. and Bunney, B. *J. of Neuroscience*, 12(6) 2433–2438 (1992).
Sakamoto, T. M.D., et al., *Surgery*, 96: No. 2, pp.146–153 (1984).
Iwatsuki, K. et al., *Clin. and Exp. Pharm. and Phys.*, 18: pp. 475–481 (1991).
Blackburn, A.M., et al., *The Lancet*, pp. 987–989 (1980).
Feurle, G. and Niestroj S., *Pancreas*, 6: No. 2 pp. 202–207 (1991).
Helmstaedter, V. et al., *Histochemistry*, 53: pp. 35–41 (1977).
Cain, G.A., et al., *203rd Nat'l. Mtg. Amer. Chem. Soc.*, Med. Chem. Paper Nos. 81 and 84, San Francisco, CA on Apr. 5–10, 1992.
Nemeroff, C., *Psychoneuroendocrinology*, 11: No. 1, pp. 15–37 (1986).
Rivest and Marsden, *Neuroscience*, 47: No. 2, pp. 341–349 (1992).
Kasckow and Nemeroff, *Reg. Peptides*, 36: pp. 153–164 (1991).
*Scrip World Pharmaceutical News*, No. 1776, Dec. 4, (1992).
G.P. Reynolds, Developments in the drug treatment of schizophrenia, *Trends in Pharmaceutical Sciences*, 13, pp. 116–121 (1992).
M. Goldstein and A. Y. Deutch, Dopaminergic mechanisms in the pathogenesis of schizophrenia, *FASES J.*, 6, pp. 2413–2421 (1992).

(List continued on next page.)

*Primary Examiner*—Emily Bernhardt
*Attorney, Agent, or Firm*—Valerie J. Camara; Mark R. Daniel

[57] ABSTRACT

Novel substituted phthalazinones of the formula (I)

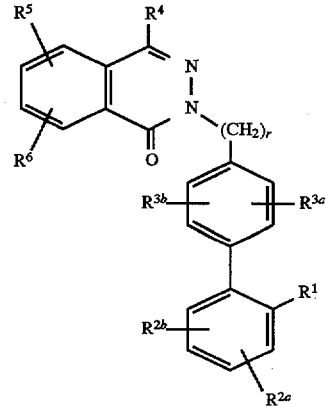

are useful as neurotensin antagonists.

6 Claims, No Drawings

OTHER PUBLICATIONS

P. W. Kalivas, Neurotransmitter regulation of dopamine neurons in the ventral tegmental area, *Brain Research Review*, 18, pp. 75–113 (1993).

U.S. application No. 07/826,710, Chakravarty et al., filed Jan. 28, 1992.

U.S. application No. 07/826,706, Chakravarty et al., filed Jan. 28, 1992.

U.S. application No. 07/826,705, Chakravarty et al., filed Jan. 28, 1992.

U.S. application No. 07/827,126, Chakravarty et al., filed Jan. 28, 1992.

SUBSTITUTED PHTHALAZINONES AS NEUROTENSIN ANTAGONISTS

This application is a U.S. national phase application based on PCT international application PCT/US93/10386 filed on Oct. 28, 1993, which is a continuation of U.S. Ser. No. 07/970,358 filed Nov. 2, 1992 (now abandoned), priority of which is claimed hereunder.

INTRODUCTION OF THE INVENTION

This invention relates to novel substituted phthalazinone compounds represented by formula I:

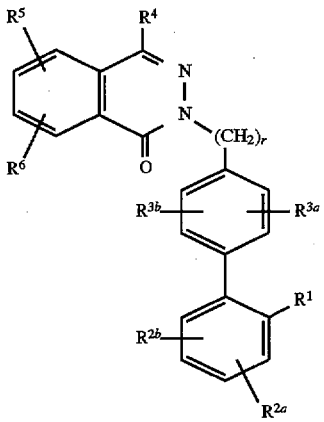

which are antagonists of peptide hormone neurotensin. The invention is also concerned with the use of aforementioned neurotensin antagonists in the treatment of states meditated by neurotensin.

BACKGROUND OF THE INVENTION

Neurotensin (NT) is a tridecapeptide hormone (pGlu-Leu-Tyr-Glu-Asn-Lys-Pro-Arg-Arg-Pro-Tyr-Ile-Leu-OH), originally isolated from the bovine hypothalamus [Carraway, R. and Leeman, S. E., *J. Biol. Chem.*, 248, 6854 (1973)], has subsequently been shown to be distributed in the brain [Uhl, G. R., et al., *Proc. Natl. Acad. Sci. USA*, 74, 4059–4063 (1977)], gastrointestinal tract [1). Kitabgi, P., Carraway, R. and Leeman, S. E., *J. Biol. Chem.*, 251, 7053 (1976); 2). Carraway, R., Kitabgi, P., and Leeman, S. E., J. Biol. Chem., 253, 7996 (1978); 3).Helmstadler, V., Taugner, C., Feurle, G. E. and Frossman, W. G., *Histochemistry*, 53, 35–41 (1977)] and pancreas [Feurle, G. E. and Niestroj, S., Pancreas, 6, 202–207 (1991) and references cited therein] of various animals including human [Mai, J. K., et al., *Neuroscience*, 22, 499–524 (1987)]. Although the physiological role of neurotensin has not yet been clearly understood, this endogenous peptide participates in a wide spectrum of central [1). Prange, A. J. and Nemeroff, C. B., *Annal. NY Acad. Sciences*, 400, 368–375 (1982); 2). Stowe, Z. N.and Nemeroff, C. B., *Life Sci.*, 49, 987–1002; (1991); 3) Kitabgi, P., *Neurochem. Int.*, 14, 111–119 (1989); 4). Levant and Nemeroff, C. B., Current topics in *Neuroendocrinology*, 8, 231–262 (1988)] and peripheral [Leeman, S. E., Aronin, N. and Ferris, C., *Hormone Res.*, 38, 93–132 (1982)] biological functions.

Neurotensin is also known to release mast cell histamine, indicating that antagonists will be useful in the treatment of allergic and inflammatory conditions, as well. [See, Rossei, S. S. and Miller, R. J., *Life Sci.*, 31, 509–516 (1982) and Kurose, M. and Saeki, K., *Eur. J. Pharmacol.*, 76, 129–136 (1981).]

Neurotensin, like most other peptides, is unable to cross the blood-brain barrier (BBB). However, certain peripheral effects of neurotensin have been observed after central administration of the peptide [Prange, A. J. and Nemeroff, C. B., *Annal. NY Acad. Sciences*, 400, 368–391 (1982)]. The direct application of neurotensin into the brain causes hypothermia, potentiation of barbiturate induced sedation, catalepsy. antinociception, blockade of psychostimulant-induced locomotor activity and reduced food consumption. In the central nervous system (CNS), neurotensin behaves as a neurotransmitter or neuromodulator [1) Uhl, G. R. and Snyder, S. H., *Eur. J. Pharmacol.*, 41, 89–91 (1977); 2) Uhl, G. R., *Annal. NY Acad. Sciences*, 400, 132–149 (1982)], and has been shown to have close anatomical and biochemical associations with the dopaminergic (DA) system [Nemeroff, C. B., et al. *Annal. NY Acad. Sciences*, 400, 330–344 (1982)]. Neurotensin increases the synthesis and the turnover of DA in rat brain. Acute and chronic treatment with clinically efficacious antipsychotic drugs (e.g., haloperidol, chloropromazine) have consistently demonstrated an increase in neurotensin concentrations in the nucleus accumbens and striatum while phenothiazines that are not antipsychotics did not produce this increase. Behaviorally, neurotensin, after central administration, mimics the effects of systemically administered neuroleptics. However, unlike classical neuroleptics (which primarily acts on $D_2$ receptors), neurotensin fails to bind to dopamine receptors or inhibit cAMP accumulation following DA receptor activation. Neurotensin does not block the stereotypy induced by DA agonists. The post-mortem studies of patients with schizophrenia showed an increase in the level of neurotensin in the Brodman's area 32 of human brain [Nemeroff, C. B., et. al., *Science.*, 221, 972–975 (1983) and references cited therein], which suggest possible roles of neurotensin in the pathophysiology of this disease. Neurotensin receptors have also been implicated in Parkinson's disease and progressive supranuclear palsy [Chinaglia, G. et al., *Neuroscience*, 39, 351–360 (1990)].

Of the total body neurotensin in many mammalian species, more than 80% is present in the gastrointestinal tract, especially in the distal small intestine in the endocrine like N-cells. In the gut, neurotensin stimulates pancreatic secretion [Sakamoto, T.,et al, *Surgery*, 96, 146–53 (1984)], inhibits gastric acid secretion and gastric emptying [Blackburn, A. M., *Lancet*, 1, 987–989 (1980)]. Neurotensin also stimulates the growth of small intestinal mucosa in an isolated defunctional loop of jejunum, which suggests a direct systemic effect of neurotensin in the gut. In addition, neurotensin can stimulate pancreatic exocrine secretion in mammals [Iwatsuki, K., et al., *Clin. Expt. Pharmacol. Physiol.*, 18, 475–481 (1991) and references cited therein].

From the structural work, it is evident that the biological activity of neurotensin resides within the carboxy terminal five or six amino acid residues. The C-terminal hexapeptide $NT^{8-13}$ has displayed full biological activity of the tridecapeptide. In contrast, all amino terminal partial sequences are essentially inactive [Leeman, S. E. and Carraway, R. E., *Annal. NY Acad. Sciences*, 400, 1–16 (1982)]. The C-terminal COOH group and two Arg residues are essential for the biological activity of $NT^{8-13}$ as well as neurotensin. L-amino acids are required at positions-9, 10, 11 and 13, and only $Arg^8$ can be replaced by D-Arg without loss of any activity. At the position-11, an aromatic amino acid is essential. Similarly, alkyl side-chains of $Ile^{12}$ and $Leu^{13}$ are also necessary for full biological activity [Kitabgi, P., *Annal. NY Acad. Sciences*, 400, 37–53 (1982)]. Most of the analogues of neurotensin examined generally behaved as agonists. However, two analogues D-Trp[11]-NT and Tyr(Me)[11]-NT have displayed partial antagonist activity [Rioux, F. R., et al., *Eur. J. Pharmacol.*, 66, 373–379 (1980)].

Although there are reports of peptidic neurotensin antagonists, none are clinically useful, due to their short biological half life and limited oral bioavailability.

A European Patent Application, EP 477,049, disclosing 3-carboxamido-1,2-pyrazoles as non-peptidic neurotensin antagonists recently published.

DETAILED DESCRIPTION OF THE INVENTION

This invention relates to novel compounds of structural formula I:

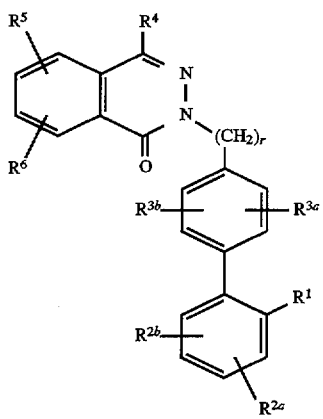

or a pharmaceutically acceptable salt thereof, wherein:

$R^1$ is:
(a) —NHSO$_2$NHCOR$^9$,
(b) —NHCONHSO$_2$R$^9$,
(c) —SO$_2$NHR$^9$,
(c) —SO$_2$NHCOR$^9$,
(d) —SO$_2$NHCONR$^7$R$^9$, or
(f) —SO$_2$NHCOOR$^9$;

$R^{2a}$ and $R^{2b}$ are each independently:
(a) H,
(b) Cl, Br, I, F,
(c) CF$_3$,
(d) C$_1$–C$_6$-alkyl,
(e) C$_1$–C$_6$-alkoxy,
(f) C$_1$–C$_6$-alkyl-S—,
(g) C$_2$–C$_6$-alkenyl,
(h) C$_2$–C$_6$-alkynyl,
(i) C$_3$–C$_7$-cycloalkyl,
(j) aryl, as defined in R$^4$ (c) below, or
(k) aryl-C$_1$–$_{C6}$-alkyl as defined in R$^4$ (c) below;

aryl is defined as phenyl or naphthyl, either unsubstituted or substituted with one or two substituents selected from the group consisting of Cl, F, Br, I, N(R$^7$)$_2$, NR$^7$COOR$^9$, NR$^7$CONR$^7$R$^9$, CO$_2$R$^7$, CONR$^7$R$^9$, C$_1$–C$_4$-alkyl, —(C$_1$–C$_4$)alkyl-Y, NO$_2$, OH, CF$_3$, C$_1$–C$_4$-alkoxy, —S(O)$_x$—(C$_1$–C$_4$)alkyl, and —(C$_1$–C$_4$) alkyl-N-(CH$_2$-CH$_2$)$_2$Q, $R^{3a}$ is:
(a) H,
(b) Cl, Br, I, F,
(c) C$_1$–C$_6$-alkyl,
(d) C$_1$–C$_6$-alkoxy, or
(e) C$_1$–C$_6$-alkoxyalkyl;

$R^{3b}$ is:
(a) H,
(b) Cl, Br, I, F,
(c) C$_1$–C$_6$-alkyl,
(d) C$_3$–C$_7$-cycloalkyl,
(e) C$_1$–C$_6$-alkoxy,
(f) CF$_3$,
(g) C$_2$–C$_6$-alkenyl, or
(h) C$_2$–C$_6$-alkynyl;

$R^4$ is:
(a) H,
(b) C$_1$–C$_6$-alkyl optionally substituted with a substituent selected from the group consisting of: C$_1$–C$_4$-alkoxy, aryl, heteroaryl, —CON(R$^{10}$)$_2$, —N(R$^{10}$)$_2$, —O—COR$^{10}$ and —COR$^{10}$ or
(c) aryl,
(d) heteroaryl, as defined in R$^4$ (c) above
(e) C$_3$–C$_7$-cycloalkyl, or
(f) —COaryl;

heteroaryl is defined as thiazolyl, imidazolyl, pyrazolyl, oxazolyl, isoxazolyl, pyridinyl, thiazinyl, quinolinyl, isoquinolinyl, phthalazinyl, quinazolinyl, pyridazinyl, pyrazinyl, or pyrimidinyl and wherein the heteroaryl is unsubstituted or substituted with one or two substituents selected from the group consisting of: —OH, —SH, —C$_1$–C$_4$-alkyl, —C$_1$–C$_4$-alkoxy, —CF$_3$, Cl, Br, F, I, —NO$_2$, —CO$_2$H, —CO$_2$-(C$_1$–C$_4$-alkyl), —NH$_2$, —NH(C$_1$–C$_4$-alkyl) and —N(C$_1$–C$_4$-alkyl)$_2$, NR$^7$COOR$^9$ and NR$^7$CONR$^7$R$^9$, Q is: a single bond, —CH$_2$—, O, NR$^7$, or S(O)$_x$;
Y is: COOR$^9$, CN, NR$^7$COOR$^9$ or CONR$^7$R$^9$;
$R^5$ and $R^6$ are independently:
(a) H,
(b) C$_1$–C$_6$-alkyl, unsubstimted or substituted with a substituent selected from the group consisting of: —OH, -guanidino, C$_1$–C$_4$-alkoxy, —N(R$^7$)$_2$, COOR$^7$, —CON(R$^7$)$_2$, —)—COR$^7$, -aryl, as defined in R$^4$ (c) above -heteroaryl, —S(O)$_x$-R$^9$, -tetrazol-5-yl, —CONHSO$_2$R$^9$, —SO$_2$NH-heteroaryl, as defined in R$^4$ (d) above —SO$_2$NHCOR$^9$, —PO(OR$^7$)$_2$, —PO(OR$^8$)R$^7$, —SO$_2$NH—CN, —NR$^8$COOR$^9$, morpholino,

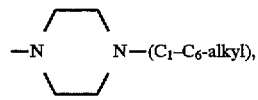

and —COR$^7$,
(c) —CO-aryl,
(d) —C$_3$–C$_7$-cycloalkyl,
(e) Cl, Br, I, F,
(f) —OH,
(g) —OR$^9$,
(h) —C$_1$–C$_4$-perfluoroalkyl,
(i) —S(O)$_x$—R$^9$,
(j) —COOR$^7$,
(k) —SO$_3$H,
(l) —NR$^7$R$^9$,
(m) —NR$^7$COR$^9$, (n) —NR⁷COOR⁹,
(o) —SO₂NR⁷R⁸,
(p) —NO₂,
(q) —NR⁷SO₂R⁹,
(r) —NR⁷CONR⁷R⁹,
(s) —OCONR⁹R⁷,
(t) -aryl, as defined in R⁴ (c) above
(u) —NHSO₂CF₃,
(v) —SO₂NH-heteroaryl, as defined in R⁴ (d) above
(w) —SO₂NHCOR⁹,
(x) —CONHSO₂R⁹,
(y) —PO(OR⁷)₂,
(z) —PO(OR⁸)R⁷,
(aa) -tetrazol-5-yl,
(bb) —CONH(tetrazol-5-yl),
(cc) —COR⁷,
(dd) —SO₂NHCN,
(ee) —CO-heteroaryl, as defined in R⁴ (d) above
(ff) —NR⁷SO₂NR⁹R⁷,
(gg) —N[CH₂CH₂]₂NR¹¹,
(hh) —N[CH₂CH₂]₂O, or
(ii) -heteroaryl; as defined in R⁴ (d) above
x is: 0, 1, or 2,
R⁷ is: H, C₁–C₅-alkyl, aryl, or —CH₂-aryl, as defined in R⁴ (c) above;
R⁸ is: H, or C₁–C₄-alkyl;
R⁹ is:
(a) aryl, as defined in R⁴ (c) above
(b) heteroaryl, as defined in R⁴ (d) above
(c) C₃–C₇-cycloalkyl,
(d) C₁–C₈-alkyl, wherein alkyl is unsubstituted or substituted with one or two substituents selected from the group consisting of: aryl, as defined in R⁴ (c) above, heteroaryl, as defined in R⁴ (d) above, —OH, —SH, C₁–C₄-alkyl, —O(C₁–C₄-alkyl), —S(C₁–C₄-alkyl), —CF₃, Cl, Br, F, I, —NO₂, —CO₂H, —CO₂—C₁—C₄-alkyl, —NH₂, —NR⁷CO₂R¹⁰, —NH(C₁–C₄-alkyl), —N(C₁–C₄-alkyl)₂, —PO₃H₂, —PO(OH)(O—C₁–C₄-alkyl), —PO(OR⁸)R⁷, —NR⁷COR¹⁰, —CONR⁷R¹⁰, —OCONR⁷R¹⁰, —SO₂NR⁷R¹⁰, —NR⁷SO₂R¹⁰, —N(CH₂—CH₂)₂Q and —CON(CH₂—CH₂)₂Q or
(e) perfluoro-C₁–C₄-alkyl;
R¹⁰ is:
(a) aryl, as defined in R⁴ (c) above,
(b) heteroaryl, as defined R⁴ (d) above,
(c) C₁–C₆-alkyl, wherein alkyl is unsubstituted or substituted with a substituent selected from the group consisting of: aryl, as defined in R⁴ (c) above, heteroaryl, as defined in R⁴ (d) above, —OH, —NH₂, —NH(C₁–C₄-alkyl), —N(C₁–C₄-alkyl)₂, —CO₂R⁷, Cl, Br, F, I, and —CF₃, or
(d) perfluoro-C₁–C₄-alkyl;
R¹¹ is: C₁–C₆-alkyl, C₃–C₇-cycloalkyl, —CONR⁷R⁸, heteroaryl, as defined in R⁴ (d) above, phenyl, —CO—C₃–C₇-cycloalkyl, or —CO—C₁–C₆-alkyl; and
r is: 1 or 2.

One embodiment of the compounds of formula (I) are those compounds wherein:
R¹ is:
(a) —NHSO₂NHCOR⁹, or
(b) —NHCONHSO₂R⁹;

R²ᵃ is: H;
R²ᵇ is: H, F, Cl, CF₃, C₁–C₆-alkyl, C₂–C₄-alkenyl, or C₂–C₄-alkynyl, aryl, wherein aryl is as defined above or aryl-C₁–C₆-alkyl;
R³ᵃ is: H;
R³ᵇ is: H, F, Cl, CF₃, C₁–C₄-alkyl, C₂–C₄-alkenyl, C₂–C₄-alkynyl, or C₅–C₆-cycloalkyl;
R⁵ and R⁶ are each independently:
(a) H,
(b) C₁–C₆-alkyl unsubstimted or substituted with COOR⁷, OCOR⁷, OH, or aryl wherein aryl is as defined above,
(c) —OH,
(d) —NO₂,
(e) —NHCOR⁹,
(f) —C₁–C₄-alkoxy,
(g) —NHCO₂R⁹,
(h) —NR⁷R⁹,
(i) —Cl, F, Br,
(j) —CF₃,
(k) —CO₂R⁷,
(l) —CO-aryl, wherein aryl is as defined above,
(m) —S(O)ₓ—C₁–C₄-alkyl,
(n) —SO₂—NH—C₁–C₄-alkyl,
(o) —SO₂—NH-aryl,
(p) —NHSO₂CH₃,
(q) -aryl, wherein aryl is as defined above,
(r) —NHCONR⁷R⁹,
(s) N[CH₂CH₂]₂NR¹¹, or
(t) —N[CH₂CH]₂O;
r is 1.

A class of this embodiment are those compounds of Formula (I) wherein:
R¹ is:
(a) —NHSO₂NHCOR⁹, or
(b) —NHCONHSO₂R⁹;
R⁴ is: H, (C₁–C₆)-alkyl, aryl, wherein aryl is as defined above, aryl-(C₁–C₆)-alkyl, or heteroaryl, wherein heteroaryl is as defined above as defined before; and
R⁵ and R⁶ are each independently: H, —C₁–C₄-alkyl, aryl, wherein aryl is as defined above, —NO₂, —NR⁷R⁹, —NHCOOR⁹, —Cl, —CH₂COOH, —S(O)ₓ—C₁–C₄-alkyl, NHCONR⁷R⁹, NHCOR⁹, CO₂R⁷, —F, N[CH₂CH₂]₂NR¹¹, or N[CH₂CH₂]₂O.

A second embodiment of the invention are the compounds of formula (I) wherein:
R¹ is:
(a) —SO₂NHR⁹,
(b) —SO₂NHCOR⁹,
(c) —SO₂NHCONR⁷R⁹, or
(d) —SO₂NHCOOR⁹;
R²ᵃ is: H;
R²ᵇ is: H, F, Cl, CF₃, C₁–C₆-alkyl, C₂–C₄-alkenyl, or C₂–C₄-alkynyl, aryl or aryl-C₁–C₆-alkyl, wherein aryl is as defined above
R³ᵃ is: H;
R³ᵇ is: H, F, Cl, CF₃, C₁–C₄-alkyl, C₂–C₄-alkenyl, C₂–C₄-alkynyl, or C₅–C₆-cycloalkyl;
R⁵ and R⁶ are independently:
(a) H,
(b) C₁–C₆-alkyl unsubstimted or substituted with COOR⁷, OCOR⁷, OH, or aryl, wherein aryl is as defined above,
(c) —OH, (d) —$NO_2$,
(e) —$NHCOR^9$,
(f) —$C_1$-$C_4$-alkoxy,
(g) —$NHCO_2R^9$,
(h) —$NR^7R^9$,
(i) —Cl, F, Br,
(j) —$CF_3$,
(k) —$CO_2R^7$,
(l) —CO-aryl wherein aryl is as defined above,
(m) —$S(O)_x$—$C_1$-$C_4$-alkyl,
(n) —$SO_2$—NH—$C_1$-$C_4$-alkyl,
(o) —$SO_2$—NH-aryl wherein aryl is as defined above,
(p) —$NHSO_2CH_3$,
(q) -aryl, wherein aryl is as defined above,
(r) —$NHCONR^7R^9$,
(s) —$N[CH_2CH_2]_2NR^{11}$, or
(t) —$N[CH_2CH_2]_2O$; and r is: 1.

A class of this embodiment are those compounds of Formula (I) wherein:

$R^1$ is:

(a) —$SO_2NHR^9$,
(b) —$SO_2NHCOR^9$,
(c) —$SO_2NHCONR^7R^9$, or
(d) —$SO_2NHCOOR^9$;

$R^4$ is: H, ($C_1$-$C_6$)alkyl, aryl, wherein aryl is as defined above, aryl-($C_1$-$C_6$)alkyl, or heteroaryl wherein heteroaryl is as defined above; and $R^5$ and $R^6$ are each independently: H, —$C_1$-$C_4$-alkyl, -aryl, wherein aryl is as defined above —$NO_2$, —$NR^7R^9$, —$NHCOOR^9$, Cl, —$CH_2COOH$, —$S(O)_x$—$C_1$-$C_4$-alkyl, $NHCONR^7R^9$, $NHCOR^9$, $CO_2R^7$, —F, $N[CH_2CH_2]_2NR^{11}$, or $N[CH_2CH_2]_2O$).

Further exemplifying this class are the compounds indicated in Table I below.

TABLE I

| Cmpd. # | $R^4$ | $R^5$ | $R^6$ | $R^9$ |
|---|---|---|---|---|
| 1 | H | H | H | —$(CH_2)_5NHBoc$ |
| 2 | H | H | H | —$(CH_2)_5NH_2$ |
| 3 | Methyl | H | H | —$(CH_2)_5NHBoc$ |
| 4 | Methyl | H | H | —$(CH_2)_5NH_2$ |
| 5 | n-Propyl | H | i-propyl | —$(CH_2)_5NHBoc$ |
| 6 | n-Propyl | H | H | —$(CH_2)_5NHBoc$ |
| 7 | n-Propyl | H | H | —$(CH_2)_5NH_2$ |
| 8 | i-Propyl | H | H | -cyclopropyl |
| 9 | i-Propyl | H | H | —$(CH_2)_4NHBoc$ |
| 10 | i-Propyl | H | H | —$(CH_2)_4NH_2$ |
| 11 | Phenyl | H | H | -cyclopropyl |
| 12 | Phenyl | H | H | —$(CH_2)_5NHBoc$ |
| 13 | Phenyl | H | H | —$(CH_2)_5NH_2$ |
| 14 | Phenyl | methyl | H | —$(CH_2)_5NHBoc$ |
| 15 | Phenyl | methyl | H | —$(CH_2)_5NH_2$ |
| 16 | p-Toluyl | H | H | —$(CH_2)_5NHCOCH_3$ |
| 17 | p-Toluyl | H | methyl | —$(CH_2)_5NH_2$ |
| 18 | p-Toluyl | H | methyl | —$(CH_2)_5NHBoc$ |
| 19 | 4-Cl-Phenyl | H | H | —$(CH_2)_5NHBoc$ |
| 20 | 4-Cl-Phenyl | H | H | —$(CH_2)_5NH_2$ |
| 21 | 4-Cl-Phenyl | H | H | —$(CH_2)_4CON(CH_3)_2$ |
| 22 | 4-Cl-Phenyl | H | methyl | —$(CH_2)_5NHBoc$ |
| 23 | 4-Br-Phenyl | H | H | —$(CH_2)_5NHBoc$ |
| 24 | 4-Br-Phenyl | H | H | —$(CH_2)_5NH_2$ |
| 25 | 4-F-Phenyl | H | H | $(CH_2)_5NHBoc$ |
| 26 | 4-F-Phenyl | H | H | $(CH_2)_5NH_2$ |
| 27 | 4-OMe-Phenyl | H | H | —$(CH_2)_5NHBoc$ |
| 28 | 4-OMe-Phenyl | H | H | —$(CH_2)_5NH_2$ |
| 29 | p-Toluyl | H | H | —$(CH_2)_5NHBoc$ |

TABLE I-continued

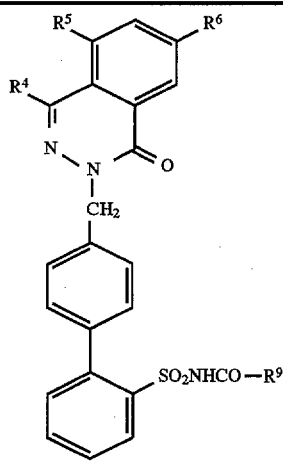

| Cmpd. # | R⁴ | R⁵ | R⁶ | R⁹ |
|---|---|---|---|---|
| 30 | p-Toluyl | H | H | (CH₂)₅NH₂ |
| 31 | p-Toluyl | H | H | (CH₂)₆NHBoc |
| 32 | p-Toluyl | H | H | (CH₂)₆NH₂ |
| 33 | p-Toluyl | H | H | —(CH₂)₃NHBoc |
| 34 | p-Toluyl | H | H | —(CH₂)₃NH₂ |
| 35 | p-Toluyl | H | H | —(CH₂)₄NHBoc |
| 36 | p-Toluyl | H | H | —(CH₂)₄NH₂ |
| 37 | p-Toluyl | H | H | —(CH₂)₆OH |
| 38 | p-Toluyl | H | H | —(CH₂)₅COOC₂H₅ |
| 39 | p-Toluyl | H | H | —(CH₂)₄COOH |
| 40 | p-Toluyl | methyl | H | —(CH₂)₅COOC₂H₅ |
| 41 | p-Toluyl | H | H | —(CH₂)₆CH₃ |
| 42 | p-Toluyl | H | H | —(CH₂)₅CONHCH₃ |
| 43 | p-Toluyl | H | H | —(CH₂)₅CON(CH₃)₂ |
| 44 | p-Toluyl | H | H | —(CH₂)₄CON(CH₃)₂ |
| 45 | p-Toluyl | H | H | —(CH₂)₄CON(CH₂)₄ |
| 46 | p-Toluyl | H | H | —(CH₂)₄CON(CH₂)₅ |
| 47 | p-Toluyl | H | H | —(CH₂)₄—CON(CH₂CH₂)₂O |
| 48 | p-Toluyl | H | H | —(CH₂)₄CON(CH₂CH₂)₂NH |
| 49 | p-Toluyl | H | H | —(CH₂)₄CON(CH₂CH₂)₂NAc |
| 50 | p-Toluyl | H | H | —(CH₂)₄CON(CH₂CH₂)₂NCH₃ |
| 51 | p-Toluyl | H | H | —(CH₂)₆CON(CH₃)₂ |
| 52 | p-Toluyl | H | H | —(CH₂)₂CH(NHBoc)COOtBu |
| 53 | p-Toluyl | H | H | -2-thienyl |
| 54 | p-Toluyl | H | H | -3-furyl |
| 55 | p-Toluyl | H | H | -2-furyl |
| 56 | p-Toluyl | H | H | —(CH₂)₂OCH₃ |
| 57 | p-Toluyl | H | H | —NH(CH₂)₃CH₃ |
| 58 | p-Toluyl | H | H | —NH(CH₂)₅CH₃ |
| 59 | p-Toluyl | H | H | —NH(CH₂)₃Cl |
| 60 | p-Toluyl | H | H | —NH(CH₂)₂-2-thienyl |
| 61 | p-Toluyl | H | H | —CH₂OCH₂CH₃ |
| 62 | p-Toluyl | H | H | —(CH₂)₅OH |
| 63 | p-Toluyl | H | H | —NH(CH₂)₅CH₃ |
| 64 | p-Toluyl | H | H | —(CH₂)₅N(CH₃)₂ |
| 65 | p-Toluyl | H | H | —(CH₂)₅NHCH₃ |
| 66 | 1-Naphthyl | H | H | —(CH₂)₅N(CH₃)₂ |
| 67 | 1-Naphthyl | H | H | —(CH₂)₅CON(CH₃)₂ |
| 68 | 1-Naphthyl | H | H | —(CH₂)₄CON(CH₃)₂ |
| 69 | 1-Naphthyl | H | H | —(CH₂)₅NHBoc |
| 70 | 1-Naphthyl | H | H | —(CH₂)₅NH₂ |
| 71 | 4-OMe-Phenyl | H | H | —(CH₂)₅CON(CH₃)₂ |
| 72 | 4-OMe-Phenyl | H | H | (CH₂)₄CON(CH₃)₂ |
| 73 | 2-Naphthyl | H | H | —(CH₂)₅N(CH₃)₂ |
| 74 | 2-Naphthyl | H | H | —(CH₂)₅CON(CH₃)₂ |
| 75 | 2-Naphthyl | H | H | —(CH₂)₄CON(CH₃)₂ |
| 76 | 2-Naphthyl | H | H | —(CH₂)₅NHBoc |
| 77 | 2-Naphthyl | H | H | —(CH₂)₅NH₂ |
| 78 | Pentamethylphenyl | H | H | —(CH₂)₅NH₂ |
| 79 | Pentamethylphenyl | H | H | —(CH₂)₅NHBoc |
| 80 | Pentamethylphenyl | H | H | —(CH₂)₄CON(CH₃)₂ |
| 81 | 2-pyridyl | H | H | —(CH₂)₄CON(CH₃)₂ |
| 82 | 4-pyridyl | H | H | —(CH₂)₄CON(CH₃)₂ |
| 83 | 2-Thienyl | H | H | —(CH₂)₄CON(CH₃)₂ |
| 84 | 2-pyridyl | H | H | —(CH₂)₅NHBoc |

TABLE I-continued

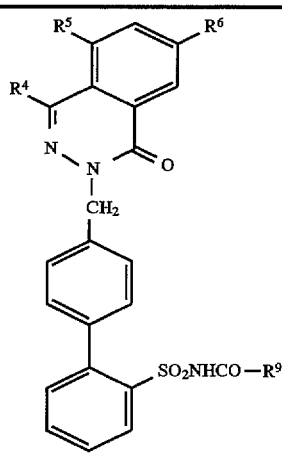

| Cmpd. # | R⁴ | R⁵ | R⁶ | R⁹ |
|---|---|---|---|---|
| 85 | 2-pyridyl | H | H | —(CH₂)₅NH₂ |
| 86 | 2-pyridyl | H | H | —(CH₂)₅N(CH₃)₂ |
| 87 | 4-pyridyl | H | H | —(CH₂)₅NHBoc |
| 88 | 4-pyridyl | H | H | —(CH₂)₅NH₂ |
| 89 | 4-pyridyl | H | H | —(CH₂)₅N(CH₃)₂ |
| 90 | 4-pyridyl | H | H | —(CH₂)₄CON(CH₃)₂ |
| 91 | 2-Thienyl | H | H | —(CH₂)₄CON(CH₃)₂ |
| 92 | 4-(N-Morpholinomethyl)-phenyl | H | H | —(CH₂)₅NHBoc |
| 93 | 4-(N-Morpholinomethyl)-phenyl | H | H | —(CH₂)₅NH₂ |
| 94 | 4-(N-Pyrrolidinomethyl)-phenyl | H | H | —(CH₂)₅NHBoc |
| 95 | 4-(N-Pyrrolidinomethyl)-phenyl | H | H | —(CH₂)₅NH₂ |
| 96 | 4-(N-Pyrrolidinomethyl)-phenyl | H | H | —(CH₂)₄CON(CH₃)₂ |
| 97 | 4-(N-Morpholinomethyl)-phenyl | H | H | —(CH₂)₄CON(CH₃)₂ |
| 98 | p-Toluyl | H | H | —(CH₂)₃CON(CH₃)₂ |
| 99 | p-Toluyl | H | H | —(CH₂)₅NHCON(CH₃)₂ |
| 100 | p-Toluyl | H | H | —(CH₂)₅NHSO₂iPr |
| 101 | p-Toluyl | H | H | —(CH₂)₃NHCON(CH₃)₂ |
| 102 | p-Toluyl | H | H | —NH(CH₂)₃CON(CH₃)₂ |
| 103 | p-Toluyl | H | H | —(CH₂)₃NHCOCH₃ |
| 104 | p-Toluyl | H | H | —(CH₂)₄CONH₂ |
| 105 | p-Toluyl | H | H | —(CH₂)₄CONHCH₃ |
| 106 | 4-Cl-Phenyl | H | H | —(CH₂)₄CON(CH₃)₂ |
| 107 | 4-F-Phenyl | H | H | —(CH₂)₄CON(CH₃)₂ |
| 108 | 2-CH₃CONH-Phenyl | H | H | —CH₂)₄CON(CH₃)₂ |

The terms "alkyl", "alkenyl", "alkynyl": and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

For a general review of synthesis and reactivity of substituted phthalazinones and related compounds, see—M. Tishler and B. Stanovnik, *Comprehensive Heterocyclic Chemistry*, Vol. 3 (part 2B), 1–56 (1984) Eds: A. J. Boulton and A. Mckillop; Pergamon Press., and also N. R. Patel, *Heterocyclic Compounds*, Vol. 27, Chapter II, pages 376–446 (1973). Ed: R. N. Castle, John Wiley & Sons, and references cited therein.

Scheme 1 illustrates the preferred method for the preparation of substituted phthalazin-1-(2H)-ones. An appropriately substituted 2-acylbenzoic acid 1 or a similar starting material is reacted with hydrazine hydrate in an appropriate solvent such as an alcohol or acetic acid under reflux for 2–24 h to form the corresponding substituted phthalazin-1-(2H)-one 2.

Scheme 1

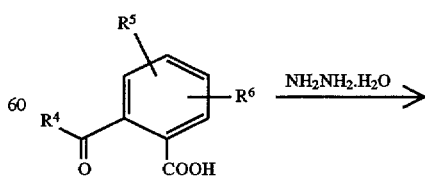

1

-continued
Scheme 1

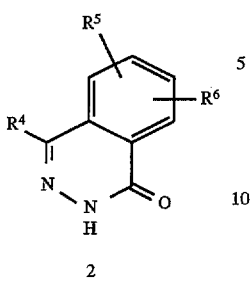

Where $R^4$ is H, alkyl or aryl, as defined before.

The keto acid 1 may be prepared from the appropriately substituted 2-bromobenzoic acid or a similar starting material using the methods described in the literature [W. E. Parham, C. K. Bradsher, K. J. Edger, *J. Org. Chem.*, 46(6), 1057(1981) and references cited therein]. Alternatively, the keto acids may also be synthesized by procedures described by R. L. Shriner et al., *J. Org. Chem.*, 16, 1064 (1951), and C. R. Hauser et al., *J. Org. Chem.*, 23, 861 (1958).

A general method for the preparation of 2-alkyl-phthalazin-1-(2H)-ones of Formula I is illustrated in Scheme 2. An appropriately substituted phthalazin-1-(2H)-one 2 is alkylated with the appropriate alkyl halide 3 (or pseudo halide, such as tosylate, mesylate, triflate and the like) in the presence of an appropriate base such as alkali metal hydrides, carbonates, bicarbonates or an organic base (e.g., trialkylamines, morpholine and the like) in an appropriate polar solvent, such as dimethylformamide, dimethylsulfoxide, tetrahydrofuran, lower alkyl alcohols and the like. The alkylated material 4 may then be transformed into the desired compound of Formula I by removal of the protecting group present in $R^{1a}$ followed by further transformation of the functional group, thus formed, into the desired $R^1$ group. Similarly, the $R^1$ a may also be directly transformed into the desired $R^1$ to give the compound of formula I.

Scheme 2

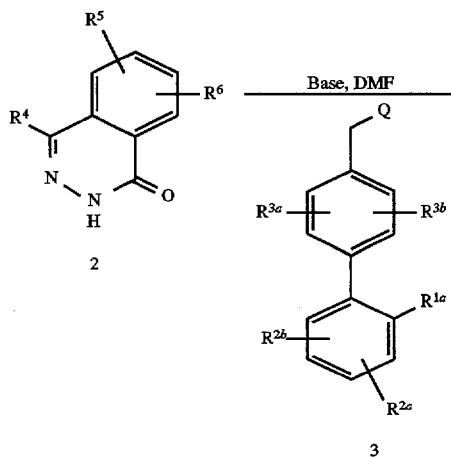

Q = Cl, Br, I, OTs etc.

-continued
Scheme 2

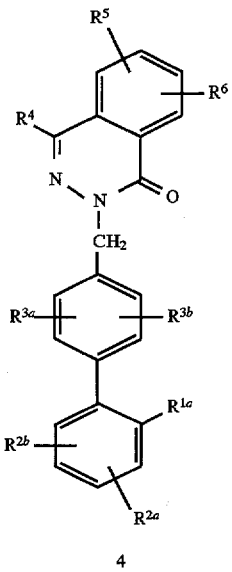

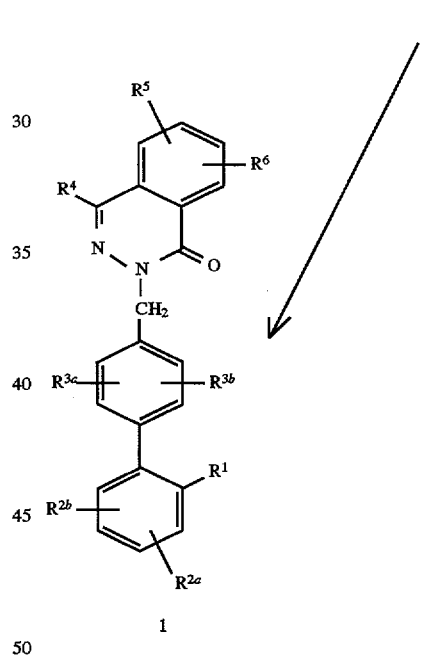

The biphenyl alkylating agents 3 can be synthesized using the reactions and techniques described in published U.S. Pat. No. 5,126,342 (Merck & Co, Inc.).

Compounds of Formula I in which $R^1$ is $SO_2NHR^9$ or $SO_2NHCOR^9$ may be prepared according to the general methods described for such transformations in U.S. Pat. No. 5,126,342. More specifically these compounds may be prepared as outlined in Scheme 3.

Scheme-3

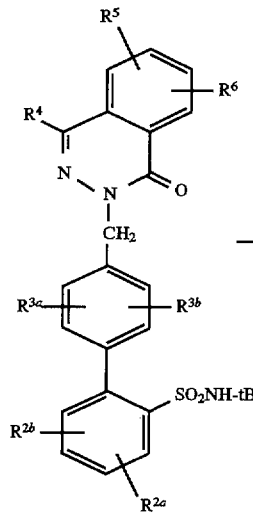

a. TFA, 25° C.-reflux
b. R⁹COOH, Carbonyldiimidazole, DBU

The protected sulfonamide 5 (prepared as described in Scheme 2 using the alkylating agent 3, where $R^{1a}$ is —SO$_2$NH-tBu) is reacted with TFA, and the resulting free sulfonamide 6 is acylated with an appropriate acylimidazole (generated from the corresponding R⁹COOH and carbonyldiimidazole) in the presence of DBU to form the acylsulfonamide 7.

Compounds of Formula I in which $R^1$ is SO$_2$NHCOOR⁹ or SO$_2$NHCONR⁷R⁹ may be prepared according to methods outlined in Schemes 4 and 5.

The sulfonamide 6 may be reacted with an appropriate isocyanate (R⁹NCO) or carbamoyl chloride (R⁷R⁹NCOCl) in the presence of an appropriate base to form the corresponding sulfonylureas 8.

Scheme-5

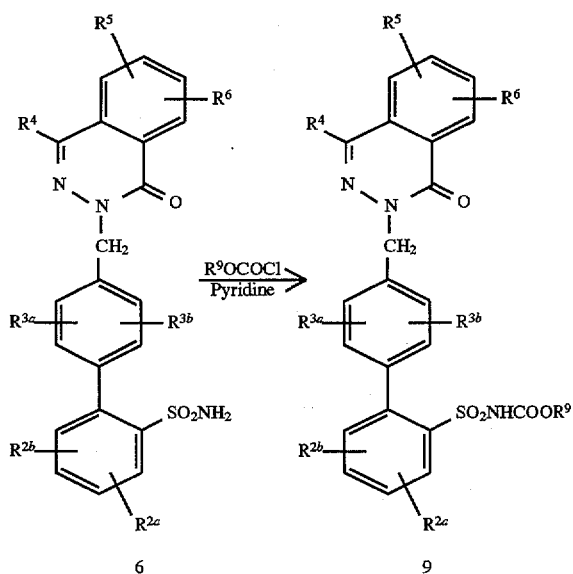

Similarly, the sulfonamide 6 may be reacted with an appropriate alkyl or aryl chloroformate ($R^9OCOCl$) in the presence of an appropriate base such as pyridine to form the corresponding sulfonylcarbamate 9.

Compounds of Formula I, where $R^1$ is —$NHSO_2NHCOR^9$ may be prepared from the corresponding nitro precursor 10 (prepared according to Scheme 2, where $R^{1a}=NO_2$) as outlined in Scheme 6. The nitro group in 10 is reduced to the corresponding amine 11 which may then be reacted with t-butylsulfamoyl chloride to give the N-t-butylsulfamide 12. Removal of the t-butyl group followed by acylation may produce the desired acylsulfamides 13. Similarly, compound 12 may be reacted with an appropriate N-acylsulfamoyl chloride to give 13.

Scheme-6

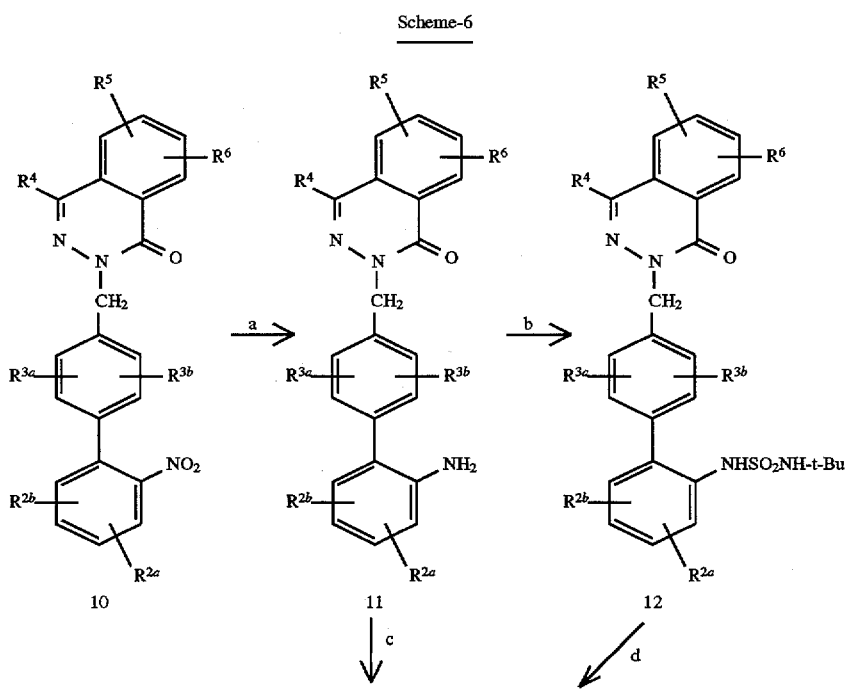

-continued
Scheme-6

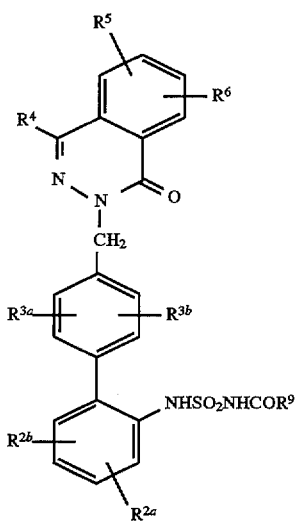

13
a. H$_2$/Pd—C or, SnCl$_2$/HCl   b. t-BuNHSO$_2$Cl   c. R$^9$CONHSO$_2$Cl
d. 1) TFA   ii) aq. NaHCO$_3$   iii) R$^9$CO—X The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glutamine salts, salts with amino acids like arginine, lysine, and the like. Also, salts with organic and inorganic acids may be prepared; e.g., HCl, HBr, H$_2$SO$_4$, H$_3$PO$_4$, methanesulfonic, toluenesulfonic, maleic, fumaric, camphorsulfonic. The nontoxic, physiologically, acceptable salts are preferred, although other salts are also useful in isolating and/or purifying the product.

The salts can be formed by conventional means, such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Neurotensin is a peptide hormone and the assays described below have been developed to identify neurotensin antagonists and to determine their efficacy in vitro. The following three assays have been employed for that purpose.

RAT FOREBRAIN RECEPTOR ASSAY

Male rats are sacrificed by decapitation following ether anesthetization. Forebrains are homogenized using a polytron in 20 volumes 50 mM Tris HCl, pH 7.4, and centrifuged at 50,000×g for 20 min. The final pellet is washed twice by rehomogenization and centrifugation as before. The final pellet is resuspended at a concentration of 8 mg tissue (wet weight) per 0.750 ml of 50 mM Tris HCl, pH 7.4, which also contains 1 mM EDTA, 4 mg/ml bacitracin, 5 mM levocabastine HCl, 1 mM phenanthroline, 10 mg/ml soybean trypsin inhibitor and 100 mM phenyl methyl sulfonyl fluoride. Assay tubes (13×100 mm polypropylene) receive 1) 100 µl buffer or 10 mM neurotensin (for non-specific binding) 2) 100 µl of 60 pM [$^{125}$I]neurotensin 3) 20 µl test compounds 4) 750 µl tissue suspension and 5) enough buffer to bring final volume to 1 ml. After 30 minutes at room temp, the samples are filtered using a Brandel M24 cell harvestor with GF/B filtermats that have been presoaked in 0.2% polyethyleneimine for 2 hours. The tubes are rinsed with 3×4 ml of ice cold 10 mM Tris buffer (pH 7.4 at room temperature). The filter discs are placed in 12×75 mm polypropylene tubes for counting on a Packard Multi-Prias gamma counter.

HUMAN HT-29 CELL MEMBRANE ASSAY

HT-29 cells were routinely grown in 225 cm$^2$ Costar tissue culture flasks at 37° C. in a humidified atmosphere of 5% CO$_2$/95% air in Dulbecco's modified Eagle's medium with high glucose containing 50 U/ml penicillin, 50 mg/ml streptomycin, 5% fetal bovine serum and 5% newborn calf serum. Cells were subcultured with 0.25% trypsin at a ratio of 1:6 with confluence being reached at 48 to 72 hrs. Cells from confluent flasks (approx. 1×108 cells/flask) were harvested by scraping. The cells were pelleted by centrifugation (1000×g, 5 min), resuspended in 50 mM Tris HCl, pH 7.4, and homogenized with a polytron (setting 7 for 10 sec.). Cell membranes were washed twice by centrifugation (50,000×g, 15 min) and rehomogenized. The resulting pellet was either frozen at −70° C. for future use or run directly in the assay by resuspending at a concentration of 0.5×106 cells per 0.750 ml of assay buffer (50 mM Tris HCl, pH 7.4, containing 1 mM EDTA, 40 mg/ml bacitracin, 1 mM phenanthroline, 10 mg/ml soybean trypsin inhibitor and 100 mM phenylmethylsulfonyl fluoride).

Assay tubes (13×100 mm polypropylene) receive 1) 100 µl buffer or 10 mM neurotensin (for non-specific binding) 2) 100 µl of 60 pM [$^{125}$I]neurotensin 3) 20 µl test compounds 4) 750 μl cell membrane suspension and 5) enough buffer to bring final volume to 1 ml. After 30 minutes at room temperature, the samples are filtered using a Brandel M24 cell harvestor with GF/B filtermats that have been presoaked in 0.2% polyethyleneimine for 2 hours. The tubes are rinsed with 3×4 ml of ice cold 10 mM Tris buffer (pH 7.4 at room temperature). The filter discs are placed in 12×75 mm polypropylene tubes for counting on a Packard Multi-Prias gamma counter. [The above assay is derived from the assay described in Kitabgi, P. et al., Molecular Pharmacology, 18, 11–19 (1980)].

NEUROTENSIN BINDING ASSAY TO HUMAN FRONTAL CORTEX

Post-mortem human brain is obtained through the National Disease Research Interchange (Philadelphia, PA). The donors were without psychiatric or neurological abnormalities. Frontal cortex is dissected free of white matter and homogenized using a polytron in 20 volumes 50 mM Tris HCl, pH 7.4, and centrifuged at 50,000×g for 20 min. The resulting pellet is washed twice by rehomogenization and centrifugation as before. The final pellet is resuspended at a concentration of 8 mg tissue (wet weight) per 0.750 ml of 50 mM Tris HCl, pH 7.4, which also contains 1 mM EDTA, 4 mg/ml bacitracin, 1 mM phenanthroline, 10 mg/ml soybean trypsin inhibitor and 100 mM phenyl methyl sulfonyl fluoride. Assay tubes (13×100 mm polypropylene) receive 1) 100 μl buffer or 10 mM neurotensin (for non-specific binding) 2) 100 μl of 60 pM [$^{125}$I]neurotensin 3) 20 μl test compounds 4) 750 μl tissue suspension and 5) enough buffer to bring final volume to 1 ml. After 30 minutes at room temp, the samples are filtered using a Brandel M24 cell harvestor with GF/B filtermats that have been presoaked in 0.2% polyethyleneimine for 2 hours. The tubes are rinsed with 3×4 ml of ice cold 10 mM Tris buffer (pH 7.4 at room temperature). The filter discs are placed in 12×75 mm polypropylene tubes for counting on a Packard Multi-Prias gamma counter.

Using the methodology described above, representative compounds of the invention were evaluated and all were found to exhibit an activity of at least $IC_{50}<50\mu M$ thereby demonstrating and confirming the utility of the compounds of the invention as effective neurotensin antagonists.

Thus, the compounds of the present invention are useful in attenuating the effect of peptide hormone neurotensin, and hence in the treatment of conditions that are caused by altered levels of neurotensin in humans. These compounds are of value in the treatment of a variety of central nervous system disorders, such as psychoses, depression, Alzheimer's disease and anxiety. These compounds may also be expected to be useful in the treatment of gastrointestinal disorders such as gastroesophageal reflux disorder (GERD), irritable bowel syndrome, diarrhea, cholic, ulcer, GI tumors, dyspepsia, pancreatitis and esophagitis.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and as such are not to be considered as limiting the invention set forth in the claims appended hereto.

All $^1$H-NMR spectra were recorded on a Varian XL-200 or XL-400 Fourier Transform spectrometer. Chemical shifts are reported as (parts per million) downfield from tetramethylsilane. Mass spectra were obtained from the Merck & Co, Inc. mass spectral facility in Rahway, N.J.. Analytical TLC was conducted on E. M. Merck precoated silica plates (0.25 mm on glass, Kieselgel 60 F254) with UV and/or iodine visualization. Flash chromatography was conducted using E. Merck silica gel (mesh 200–400). All reactions were carried out under an atmosphere of dry nitrogen under standard conditions unless specified otherwise.

EXAMPLE 1

Synthesis of Phthalazin-1(2H)-ones: (A General Description)

To a suspension or a solution of an appropriate 2-acylbenzoic acid (available from a commercial source or prepared according to the literature procedure cited earlier)(1 mMol) in ethanol (5 ml) was added hydrazine hydrate (5 mMol), and the resulting mixture was refluxed for 2–6 h. The reaction was cooled to room temperature, and the solid precipitated was filtered, washed with water and then cold ethanol. The resulting solid was dried in vacuo to give the desired phthalazin-1-(2H)-one which was crystallized from ethanol or any other appropriate solvent. Alternatively, the reaction mixture was concentrated to give the crude product which was then purified by trituration with water followed by crystallization from an appropriate solvent to give the desired phthalazin-1-(2H)-one.

Table II lists representative examples of phthalazin-1(2H) -ones prepared according to the procedure outlined in Example 1.

TABLE II

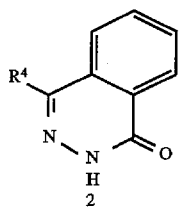

| Compound # | R[4] | Melting Point* |
|---|---|---|
| 2A | methyl | 221–222° C. (ethanol) |
| 2C | phenyl | 232–233° C. (ethanol) |
| 2D | p-toluyl | 259–260° C. (ethanol) |
| 2E | (4-Cl)phenyl | 267° C. (toluene) |
| 2F | 1-naphthyl | 261° C. (ethanol) |
| 2G | pentamethylphenyl | 276° C. |
| 2H | 2-pyridyl | $^1$H-NMR, FAB MS: 224 (M + H) |
| 2I | i-propyl | 156–157° C. (ethanol) |
| 2J | (4-OMe)phenyl | 240–241° C. |
| 2K | (4-F)phenyl | 268° C. |
| 2L | H | $^1$H-NMR, FAB MS: 147 (M + H) |

*Recrystallization solvent.

EXAMPLE 2

Preparation of 4-p-toluyl-2-(2'-aminosulfonyl) biphen-4-yl)methyl-phthalazin-1-(2H)-one.

Step 1. 4-p-toluyl-2-(2'-t-butylaminosulfonyl)-biphen-4-yl)methyl-phthalazin-1-(2H)-one (Alkylation of substituted phthalazin-1-(2H)-one)

To a suspension of 4-p-toluyl-phthalazin-1-(2H)-one [compound 2D] (2.36 g, 10 mMol) in toluene (50 mL) were added 2:5 N aqueous NaOH (4 mL) and Triton B (1 mL) followed by 2-(4'-bromomethylbiphenyl)-t-butylsulfonamide [prepared according to the procedure described in U.S. Pat. No. 5,126,342] (4.2 g, 11 mMol). The mixture was stirred at 85° C. for 12 h and then cooled to room temperature. The reaction was diluted with ethylacetate (100 mL), and the organic phase was washed with water (3×50 mL), and then dried over MgSO$_4$. The ethylacetate layer was filtered and concentrated in vacuo to a small volume (~10 mL). Dry ether (100 mL) was added and the precipitate formed was filtered and dried. The crude product was then recrystallized from hot ethylacetate to give the desired product 4-p-toluyl-2-(2'-t-butylaminosulfonyl)-biphen-4-yl)methyl-phthalazin-1-(2H)-one as white crystalline solid (4.3 g).

$^1$H-NMR (CDCl$_3$): δ 8.49 (m, 1H), 8.15 (d,1H), 7.76 (m, 3H), 7.15–7.60 (m,11H), 5.50 (s, 2H), 3.51 (s, 1H), 2.45 (s, 3H), 0.91 (s, 9H). FAB-MS: (m/e) 538 (M+H).

Step 2. 4-p-toluyl-2-(2'-aminosulfonyl)biphen-4-yl) methyl-phthalazin-1-(2H)-one (Removal of the t-butyl group):

A solution of 4-p-toluyl-2-(2'-t-butylaminosulfonyl)-biphen-4-yl)methyl-phthalazin-1-(2H)-one (2.7 g, 5.02 mMol) in trifluoroacetic acid (20 mL) was stirred at room temperature for 12–15 h. The solvent was removed in vacuo, and the residue was treated with cold aqueous saturated NaHCO$_3$. The precipitate formed was filtered and washed with water and then dried. The solid (2.4 g) was triturated with 50% ether in ethyl acetate (20 mL) at room temperature and filtered to give the desired sulfonamide 4-p-toluyl-2-(2'-aminosulfonyl)biphen-4-yl)methyl-phthalazin-1-(2H)-one as white amorphous solid (2.2 g).

$^1$H-NMR (CDCl$_3$): Δ8.49 (m, 1H), 8.15 (d,1H), 7.76 (m, 3H), 7.15–7.60 (m,11H), 5.50 (s, 2H), 3.81 (s, 2H), 2.45 (s, 3H). FAB-MS: (m/e) 482 (M+H).

Employing the procedures outlined above in Example 2, the following phthalazinone derivatives (Table III) were prepared.

Table III

TABLE III

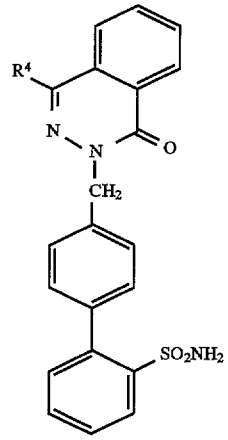

| Examples | R[4] | NMR | Mass Spect |
|---|---|---|---|
| 3 | phenyl | Yes | 468 (M + H) |
| 4 | (4-Cl)phenyl | Yes | 502, 504 (M + H) |
| 5 | pentamethylphenyl | Yes | 538 (M + H) |
| 6 | 1-naphthyl | Yes | 518 (M + H) |
| 7 | methyl | Yes | 406 (M + H) |
| 8 | n-propyl | Yes | 422 (M + H) |
| 9 | 2-pyridyl | Yes | 469 (M + H) |

EXAMPLE 10

Acylation of Sulfonamide 4-p-toluyl-2-(2'-(6-(N-t-butoxycarbonyl) aminohexanoyl)-aminosulfonyl)biphen-4-yl)methyl-phthalazin-1-(2H)-one.

To a solution of 6-(N-t-butoxycarbonyl)aminohexanoic acid (2.88 g, 12.45 mMol) in dry tetrahydrofuran (THF) (25 mL) was added carbonyl diimidazole (2.1 g, 12.45 mMol). The mixture was heated at 65° C. for 3 h. After cooling to room temperature, a solution of the sulfonamide 4-p-toluyl-2-(2'-(6-(N-t-butoxy-carbonyl)amino-hexanoyl) aminosulfonyl)biphen-4-yl)methyl-phthalazin-1-(2H)-one (obtained in Example 2) (2.0 g, 4.15 mMol) and 1,8-diazabicyclo-[5.4.0]undec-7-ene (DBU) (1.86 mL,12.45 mMol) in THF (20 mL) was added. The solution was stirred at 50° C. for 18 hr. then concentrated to dryness in vacuo. 5% Citric acid solution was added and the mixture extracted with ethyl acetate three times. The combined organic phase was washed with brine, dried (over magnesium sulfate) and the solvent removed in vacuo. The residue was pre-absorbed on silica gel and purified by flash chromatography using chloroform-methanol-NH$_4$OH (150:10:1) to give the titled acyl sulfonamide as a white amorphous solid, which was recrystallized from diethyl ether/hexane (2.3 g).

$^1$H-NMR (CDCl$_3$): δ 8.50 (m, 1H), 8.22 (d,1H), 7.78 (m, 3H), 7.15–7.60 (m,11H), 5.52 (s, 2H), 3.0 (m, 2H), 2.45 (s, 3H), 1.84 (t, 2H), 1.44 (s, 9H), 1.1–1.4 (m, 6H). FAB-MS: (m/e) 695 (M+H).

The following analogs of 4-p-toluyl-2-(2'-(6-(N-t-butoxycarbonyl)aminohexanoyl)aminosulfonyl)biphen-4-yl)methyl-phthalazin-1-(2H)-one (Table IV) were prepared by using the procedure described in Example 10.

TABLE IV

[Structure with R⁴, phthalazinone core, CH₂, biphenyl, SO₂NHCO(CH₂)₅NHBoc]

| Examples | R⁴ | NMR | Mass Spect. |
|---|---|---|---|
| 11 | phenyl | X | 681 (M + H) |
| 12 | (4-Cl)phenyl | X | 715, 717 (M + H) |
| 13 | methyl | X | 619 (M + H) |
| 14 | n-propyl | X | 647 (M + H) |

EXAMPLE 15

4-p-toluyl-2-(2'-(6-aminohexanoyl)aminosulfonyl) biphen-4-yl)methyl-phthalazin-1-(2H)-one.

To a solution of 4-p-toluyl-2-(2'-(6-(N-t-butoxycarbonyl) -aminohexanoyl)aminosulfonyl)biphen-4-yl)-methyl-phthalazin-1-(2H)-one (obtained in Example 10) (2.0 g, 2.88 mMol) in methylene chloride (10 mL) was added a saturated solution of hydrogen chloride in ethyl acetate (10 mL), and the mixture stirred at room temperature for 4 h. The volatile components of the mixture were removed in vacuo and the product was precipitated with dry ether. The hygroscopic solid was filtered, washed with dry ether and dried in vacuo. The product was then recrystallized from (methanol/ether) to give the amine hydrochloride of the titled compound (1.8 g) as white powder.

$^1$H-NMR (CD$_3$OD): δ 8.50 (m, 1H), 8.22 (d,1H), 7.78 (m, 3H), 7.15–7.60 (m,11H), 5.52 (s, 2H), 3.2 (m, 2H), 2.45 (s, 3H), 1.84 (t, 2H), 1.2 (m, 6H). FAB-MS: (m/e) 595 (M+H).

Similarly, the following analogs of 4-p-toluyl-2-(2'-(6-aminohexanoyl)aminosulfonyl)biphen-4-yl)methyl-phthalazin-1-(2H)-one (Example 15) were also prepared.

TABLE V

[Structure with R⁴, phthalazinone core, CH₂, biphenyl, SO₂NHCO(CH₂)₅NH₂]

| Examples | R⁴ | NMR | Mass spect. |
|---|---|---|---|
| 16 | phenyl | X | 581 (M + H) |
| 17 | (4-Cl)phenyl | X | 615, 617 (M + H) |
| 18 | methyl | X | 519 (M + H) |
| 19 | n-propyl | X | 547 (M + H) |

EXAMPLE 20

4-p-toluyl-2-(2'-(6-(N,N-dimethylamino)hexanoyl) aminosulfonyl)-biphen-4-yl)methyl-phthalazin-1-(2H)-one.

The amine (from Example 15) (10 mg, 0.017 mmol), 30% formaldehyde solution (1 mL) and formic acid (0.4 mL) were heated together at 100° C. for 2 hr. The mixture was concentrated to dryness in vacuo. The residue was pre-absorbed on silica gel and chromatographed (0–10% methanol/methylene chloride, 1% ammonia) to give the titled dimethylamine compound (5.9 mg, 56%) (for spectral data see Table VI).

EXAMPLE 21

4-p-toluyl-2-(2'-(4-(N-t-butoxycarboxamido) butanoyl) aminosulfonyl)-biphen-4-yl)methyl-phthalazin-1-(2H)-one.

Carbonyl diimidazole (49 mg, 0.3 mmol) was added to a solution of t-BOC-aminobutyric acid (61 mg, 0.3 mmol) in tetrahydrofuran (THF) (3 mL) under nitrogen at room temperature. The mixture was heated at 65° C. for 3 hr. After cooling to room temperature, a solution of the sulfonamide (obtained in Example 2) (48 mg, 0.1 mmol)and 1,8-diazabicyclo[5.4.0]undec-7-ene (DBU) (37 μL, 0.25 mmol) in THF (3 mL) was added. The solution was heated at 50° C. for 18 hr. then concentrated to dryness in vacuo. 5% Citric acid solution was added and the mixture extracted with ethyl acetate three times. The combined organic phase was washed with brine, dried (magnesium sulfate) and the solvent removed in vacuo. The residue was pre-absorbed on silica gel and chromatographed (0–10% methanol/ methylene chloride) to give the titled acyl sulfonamide which was recrystallized from diethyl ether/hexane (32 mg, 48%) (for spectral data see Table VI).

EXAMPLE 22

4-p-toluyl-2-(2'-(4-(N,N-dimethylcarboxamido) butanoyl)amino-sulfonyl)biphen-4-yl)methyl-phthalazin-1-(2H)-one.

The titled dimethyl amide was synthesized from the sulfonamide (Example 2) and dimethylamidobutyric acid using the procedure outlined for Example 21. Chromatography (0–5% methanol/methylene chloride) followed by recrystallization (ethyl acetate/diethyl ether) gave the desired dimethyl amide in 51% yield (for spectral data see Table VI).

EXAMPLE 23

4-p-toluyl-2-(2'-(5-ethoxycarbonyl-pentanoyl) aminosulfonyl) biphen-4-yl)methyl-phthalazin-1-(2H)-one.

The titled ethyl ester was synthesized from the sulfonamide (Example 2) and adipic acid mono-ethyl ester using the procedure outlined for Example. 21. Chromatography (0–5% methanol/methylene chloride, 0.5% ammonia) followed by recrystallization (ethyl acetate/diethyl ether) gave the desired ethyl ester in 48% yield (for spectral data see Table VII).

EXAMPLE 24

4-p-toluyl-2-(2'-(5-carboxy-pentanoyl) aminosulfonyl)biphen-4-yl)methyl-phthalazin-1-(2H)-one.

2M Lithium hydroxide solution (0.9 mL) was added to a stirred solution of the ethyl ester (Example 23) (300 mg, 0.47 mmol) in THF (15 mL) and water (3 mL) at room temperature. After stirring for 3 hr., 2M lithium hydroxide solution (0.9 mL) was added and stirring continued for 18 hr. The solution was concentrated in vacuo. 5% Citric acid was added and the mixture extracted with chloroform three times. The combined organic phase was washed with brine, dried (magnesium sulfate) and the solvent removed in vacuo to give the titled carboxylic acid (245 mg, 86%) (for spectral data see Table VII).

EXAMPLE 25

4-p-toluyl-2-(2'-(5-(N-morpholinocarbonyl) pentanoyl)aminosulfonyl)biphen-4-yl)methyl-phthalazin-1-(2H)-one.

Carbonyl diimidazole (32 mg, 0.2 mmol) was added to a stirred solution of the carboxylic acid (Example 24) (40 mg, 0.066 mmol) in THF (3 mL) under nitrogen at room temperature. The solution was heated at 65° C. for 3 hr. After cooling to room temperature, morpholine (9 µL, 0.1 mmol) was added and the mixture heated at 50° C. for 18 hr. The solution was concentrated to dryness in vacuo. 5% Citric acid solution was added and the mixture extracted with ethyl acetate three times. The combined organic phase was washed with brine, dried (magnesium sulfate) and the solvent removed in vacuo. The residue was pre-absorbed on silica gel and chromatographed (0–5% methanol/methylene chloride) to give the titled morpholino amide compound (15 mg, 33%) (for spectral data see Table VII).

EXAMPLE 26

4-p-toluyl-2-(2'-(5-(N,N-dimethylcarboxamido) pentanoyl)aminosulfonyl)biphen-4-yl)methyl-phthalazin-1-(2H)-one.

The titled dimethyl amide was synthesized from the carboxylic acid (Example 24) and dimethylamine using the procedure outlined for Example 25. Chromatography (0–3% methanol/methylene chloride) afforded the dimethyl amide (15.5 mg, 37%) (for spectral data see Table VII).

EXAMPLE 27

4-p-toluyl-2-(2'-(6-(N -acetamido)hexanoyl) aminosulfonyl)-biphen-4-yl)methyl-phthalazin-1-(2H)-one.

Acetic anhydride (0.5 mL) followed by dimethylaminopyridine (3 mg) was added to the amine hydrochloride (obtained from Example 15) (30 mg, 0.048 mmol) under nitrogen at room temperature. The solution was stirred at room temperature for 18 hr. then water added. The solid which precipitated was isolated by filtration and dried in vacuo. Recrystallization (ethyl acetate/diethyl ether) gave the titled acetamide (14.5 mg, 48%) (for spectral data see Table VII).

EXAMPLE 28

4-p-toluyl-2-(2'-(6-(N,N-dimethyl carbamoyl) hexanoyl )aminosulfonyl)biphen-4-yl)methyl-phthalazin-1-(2H)-one.

DBU (66 µL, 0.441 mmol) was added to the amine hydrochloride (Example 15) (80 mg, 0.127 mmol) in THF (3 mL) under nitrogen at 0° C. Dimethylcarbamyl chloride (17.5 µL, 0.190 mmol) was added and stirring continued at 0° C. for 3 hr. 5% Citric acid solution was added and the mixture extracted with ethyl acetate four times. The combined organic phase was washed with water, brine, dried (magnesium sulfate) and the solvent removed in vacuo. The residue was chromatographed (4% methanol/methylene chloride) to give the titled dimethyl urea (56 mg, 66%) (for spectral data see Table VII).

EXAMPLE 29

4-p-toluyl-2-(2'-(6-(N-iso-propylsulfonamido) hexanoyl)aminosulfonyl)biphen-4-yl)methyl-phthalazin-1-(2H)-one.

DBU (35 µL, 0.24 mmol) was added to the amine hydrochloride (Example 15) (50 mg, 0.08 mmol) in THF (3 mL) under nitrogen at 0° C. Iso-propylsulfonyl chloride (13 µL, 0.035 mmol) was added and stirring continued at 0° C. for 3 hr. The solution was concentrated in vacuo then 5% citric acid solution added. The mixture was extracted with ethyl acetate four times. The combined organic phase was washed with brine, dried (magnesium sulfate) and the solvent removed in vacuo. The residue was pre-absorbed on silica gel and chromatographed (0–10% methanol/methylene chloride) to give the iso-propylsulfonamide (28 mg, 50%) (for spectral data see Table VIII).

EXAMPLE 30

4-p-toluyl-2-(2'-(4-aminobutanoyl)aminosulfonyl) biphen-4-yl)methyl-phthalazin-1-(2H)-one.

A saturated solution of hydrogen chloride in ethyl acetate (1 mL) was added to the t-Boc-compound (obtained from Example 21) (61 mg, 0.091 mmol) and the mixture stirred at room temperature for 1 hr. The volatile components of the mixture were removed in vacuo and the residue recrystallized (ethyl acetate/diethyl ether) to give the titled amine as the hydrochloride salt (38 mg, 74%) (for spectral data see Table VIII).

EXAMPLE 31

4-p-toluyl-2-(2'-(4-(N,N-dimethylcarbamoyl) butanoyl)aminosulfonyl)biphen-4-yl)methyl-phthalazin-1-(2H)-one.

DBU (28 µL, 0.25 mmol) was added to the amine hydrochloride (Example 30) (45 mg, 0.07 mmol) in THF (1.5 mL)

under nitrogen at 0° C. Dimethylcarbamyl chloride (10 μL, 0.11 mmol) was added and stirring continued at 0° C. for 5 hr. The solution was concentrated in vacuo then 5% citric acid solution added. The mixture was extracted with ethyl acetate four times. The combined organic phase was washed with brine, dried (magnesium sulfate) and the solvent removed in vacuo. The residue was pre-absorbed on silica gel and chromatographed (0–10% methanol/methylene chloride) to give the titled dimethyl urea (16 mg, 36%) (for spectral data see Table VIII).

EXAMPLE 32

4-p-toluyl-2-(2'-(5-(N-pyrrolidinocarbonyl) pentanoyl)aminosulfonyl)biphen-4-yl)methyl-phthalazin-1-(2H)-one.

The titled pyrrolidine amide was synthesized from the carboxylic acid (Example 24) and pyrrolidine using the procedure outlined for Example 25. The crude product was pre-absorbed on silica gel and chromatographed (0–10% methanol/methylene chloride) to give the pyrrolidine amide (29 mg, 67%) (for spectral data see Table VIII).

EXAMPLE 33

4-p-toluyl-2-(2'-(3-(N,N-dimethylcarboxamido) propylaminocarbonyl)-aminosulfonyl)biphen-4-yl) methyl-phthalazin-1-(2H)-one.

DBU (29 μL, 0.20 mmol) followed by carbonyl diimidazole (48.8 mg, 0.30 mmol) was added to 3-(dimethylamido) butyl amine hydrochloride (50 mg, 0.30 mmol) in THF (3 mL) under nitrogen at room temperature. After stirring at room temperature for 2.5 hr., a solution of the sulfonamide (Example 2) (48 mg, 0.10 mmol) and DBU (45 μL, 0.30 mmol) was added and the mixture stirred at room temperature for a further 18 hr. The solution was concentrated in vacuo then 5% citric acid solution added. The mixture was extracted with ethyl acetate four times. The combined organic phase was washed with brine, dried (magnesium sulfate) and the solvent removed in vacuo. Recrystallization (ethyl acetate/diethyl ether) gave the titled sulfonyl urea (18 mg, 28%) (for spectral data see Table VIII).

EXAMPLE 34

4-p-toluyl-2-(2'-(hexylaminocarbonylaminosulfonyl) biphen-4-yl)methylphthalazin-1-(2H)-one DBU (37 μL, 0.25 mmol) was added to a stirred solution of the free sulfonamide (Example 2) (48 mg, 0.10 mmol) in THF (3 mL) under nitrogen at room temperature. After stirring for 0.5 hr. hexyl isocyanate (27 μL, 0.25 mmol) was added and the mixture stirred for 18 hr. The solvent was removed in vacuo then 5% citric acid solution added. The mixture was extracted with ethyl acetate three times. The combined organic phase was washed with brine, dried (magnesium sulfate) and the solvent removed in vacuo. The residue was pre-absorbed on silica gel and chromatographed (5% methanol/methylene chloride, 0.5% ammonia) to give the titled sulfonyl urea that was recrystallized from ethyl acetate/hexane (9.1 mg, 15%) (for spectral data see Table IX).

EXAMPLES 35–37

Examples 35–37 were prepared using the procedure outlined for Example 34 (See Table IX).

EXAMPLES 38–47

Examples 38–47 were prepared using appropriate procedures as outlined for Examples 1–33 (See Table IX).

TABLE VI

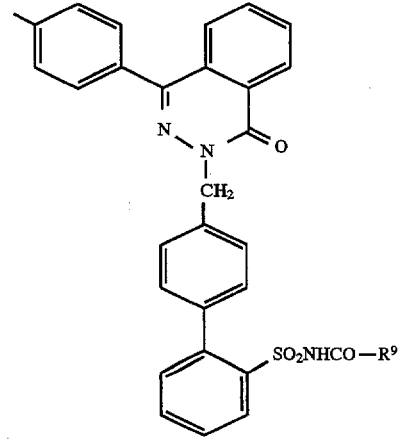

| Examples | R⁹ (NMR solvent) | Aromatic Protons | Benzyl Protons (s, 2H) | NMR Tolyl Methyl (s, 3H) | R Group Protons | MS (FAB) |
|---|---|---|---|---|---|---|
| 20 | (CH₂)₅NMe₂ | 8.45(m, 1H)<br>8.15(d, 1H)<br>7.83(m, 3H) | 5.50 | 2.44 | 3.34(m, 2H)<br>2.66(s, 6H)<br>1.84(t, 2H) | 623.4 (M + H) |
|  | (CD₃OD/CDCl₃) | 7.58–7.18(m, 11H) |  |  | 1.51(t, 2H)<br>1.24(m, 4H) |  |
| 21 | (CH₂)₃NHBoc | 8.48(m, 1H) | 5.52 | 2.44 | 2.95(m, 2H) | 669.5 |

TABLE VI-continued

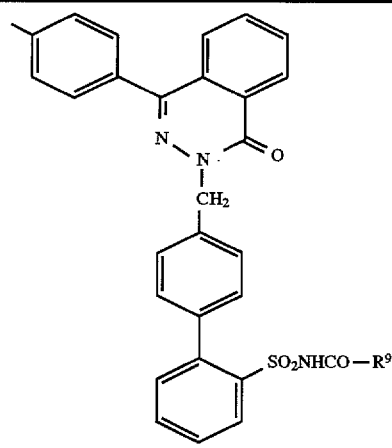

| Examples | R⁹ (NMR solvent) | Aromatic Protons | Benzyl Protons (s, 2H) | NMR Tolyl Methyl (s, 3H) | R Group Protons | MS (FAB) |
|---|---|---|---|---|---|---|
|  | (CDCl₃) | 8.23(d, 1H) 7.78(m, 3H) 7.62–7.25(m, 11H) |  |  | 1.82(t, 2H) 1.51(m, 2H) 1.41(s, 9H) | (M + H) |
| 22 | (CH₂)₃CONMe₂ (CDCl₃) | 8.49(m, 1H) 8.25(d, 1H) 7.79(m, 3H) 7.62–7.26(m, 11H) | 5.51 | 2.44 | 2.89(s, 3H) 2.87(s, 3H) 2.21(t, 2H) 1.93(t, 2H) 1.66(m, 2H) | 623.9 (M + H) |

TABLE VII

| Examples | R⁹ (NMR solvent) | Aromatic Protons | Benzyl Protons (s, 2H) | NMR Tolyl Methyl (s, 3H) | R Group Protons | MS (FAB) |
|---|---|---|---|---|---|---|
| 23 | (CH₂)₄COOEt (CDCl₃) | 8.50(m, 1H) 8.25(d, 1H) 7.80(m, 3H) 7.60–7.24(m, 11H) | 5.51 | 2.45 | 4.07(q, 2H) 2.12(t, 2H) 1.80(t, 2H) 1.37(m, 4H) 1.20(t, 3H) | 638.4 (M + H) |
| 24 | (CH₂)₄COOH (CDCl₃) | 8.50(m, 1H) 8.26(m, 1H) 7.81(m, 3H) 7.61–7.24(m, 11H) | 5.57 | 2.45 | 2.31(t, 2H) 1.93(t, 2H) 1.61(m, 2H) 1.45(m, 2H) | 610.4 (M + H) |
| 25 | (CH₂)₄CON⟨O⟩ (CDCl₃) | 8.48(m, 1H) 8.25(d, 1H) 7.80(m, 3H) 7.60–7.25(m, 11H) | 5.50 | 2.44 | 3.65(m, 4H) 3.56(m, 2H) 3.36(m, 2H) 2.16(t, 2H) 1.86(t, 2H) 1.39(m, 4H) | 679.5 (M + H) |
| 26 | (CH₂)₄CONMe₂ (CDCl₃) | 8.50(m, 1H) 8.25(d, 1H) 7.81(m, 3H) 7.62–7.24(m, 11H) | 5.50 | 2.44 | 2.91(s, 3H) 2.89(s, 3H) 2.16(t, 2H) 1.87(t, 2H) 1.40(m, 4H) | 637.0 (M + H) |
| 27 | (CH₂)₅NHCOMe (CDCl₃) | 8.48(m, 1H) 8.24(d, 1H) 7.80(m, 3H) 7.64–7.25(m, 11H) | 5.51 | 2.44 | 3.12(m, 2H) 1.91(s, 3H) 1.77(t, 2H) 1.34(m, 4H) 1.11(m, 2H) | 637 (M + H) |
| 28 | (CH₂)₅NHCONMe₂ (CD₃OD/CDCl₃) | 8.44(m, 1H) 8.17(d, 1H) 7.83(m, 3H) 7.65(m, 11H) | 5.51 | 2.43 | 3.02(m, 2H) 2.82(s, 6H) 1.78(t, 2H) 1.31(m, 4H) 1.08(m, 2H) | 665.9 (M + 1) |

TABLE VIII

| Examples | R⁹ (NMR solvent) | Aromatic Protons | Benzyl Protons (s, 2H) | NMR Tolyl Methyl (s, 3H) | R Group Protons | MS (FAB) |
|---|---|---|---|---|---|---|
| 29 | (CH₂)₅NHSO₂iPr (CDCl₃) | 8.48(m, 1H) 8.24(d, 1H) 7.80(m, 3H) 7.62–7.24(m, 11H) | 5.52 | 2.45 | 4.45(m, 1H) 3.04(m, 2H) 1.76(t, 2H) 1.43(m, 2H) 1.35(m, 2H) 1.33(d, 6H) 1.18(m, 2H) | 701 (M + H) |
| 30 | (CH₂)₃NH₂.HCl (CD₃OD) | 8.46(m, 1H) 8.16(d, 1H) 7.92–7.85(m, 3H) 7.67–7.30(m, 11H) | 5.54 | 2.46 | 2.79(t, 2H) 1.93(t, 2H) 1.67(m, 2H) | 567.8 (M + H) |
| 31 | (CH₂)₃NHCONMe₂ (CDCl₃) | 8.47(m, 1H) 8.25(d, 1H) 7.77(m, 3H) 7.57–7.26(m, 11H) | 5.54 | 2.44 | 3.05(m, 2H) 2.80(s, 6H) 1.85(t, 2H) 1.53(m, 2H) | 638.2 (M + H) |
| 32 | (CH₂)₄CON⟨pyrrolidine⟩ (CDCl₃) 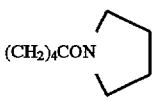 | 8.48(m, 1H) 8.25(d, 1H) 7.76(m, 3H) 7.57–7.36(m, 11H) | 5.50 | 2.44 | 3.40(t, 2H) 3.31(t, 2H) 2.13(t, 2H) 1.89(m, 4H) 1.86(m, 2H) 1.39(m, 4H) | 663.2 (M + H) |
| 33 | NH(CH₂)₃CONMe₂ (CDCl₃) | 8.48(m, 1H) 8.16(d, 1H) 7.77(m, 3H) 7.56–7.26(m, 11H) | 5.50 | 2.44 | 3.08(m, 2H) 2.91(s, 3H) 2.88(s, 3H) 2.18(t, 2H) 1.69(m, 2H) | 638.3 (M + H) |

TABLE IX

| Examples | R⁹ | Nmr Spectrum | MS (FAB) |
|---|---|---|---|
| 34 | NH(CH₂)₅CH₃ | X | 581.8 (M + H) |
| 35 | NH(CH₂)₃CH₃ | X | 609.6 (M + H) |
| 36 | NH(CH₂)₃Cl | X | 601.8 (M + H) |
| 37 | NH(CH₂)₂-2-Thienyl | X | 635.3 (M + H) |
| 38 | (CH₂)₂CH-(COOtBu)NHBoc | X | 768.2 (M + H) |
| 39 | 2-Thienyl | X | 592.6 (M + H) |
| 40 | 3-Furyl | X | 576.8 (M + H) |
| 41 | (CH₂)₂OCH₃ | X | 568.8 (M + H) |
| 42 | 2-Furyl | X | 576.7 (M + H) |
| 43 | CH₂OCH₂CH₃ | X | 568.8 (M + H) |
| 44 | (CH₂)₅OH | X | 596.9 (M + H) |
| 45 | (CH₂)₃NHCOMe | X | 609.6 (M + H) |
| 46 | (CH₂)₄CONH₂ | X | 609.5 (M + H) |
| 47 | (CH₂)₄CONHMe | X | 623.5 (M + H) |

EXAMPLE 48

Step 1: 4-(Morpholinomethyl)phenyl-2-[(2'-t-butylamino-sulfonyl)biphen-4-yl]methyl-phthalazin-1-(2H)-one.

A mixture of 4-p-toluyl-2-[(2'-t-butylaminosulfonyl)-biphen-4-yl]methyl-phthalazin-1-(2H)-one (0.27 g, 0.5 mMol), N-bromo-succinimide (0.09 g, 0.5 mMol) and azaisobutyro-nitrile (AIBN) (0.01 g) was refluxed for 3 h and then cooled down to room temperature. The mixture was filtered and the filtrate concentrated in vacuo to give a foam (0.3 g). The foam was dissolved in methylene chloride (5 mL) and cooled in an ice-bath. Morpholine (1 mL) was then added, and the mixture was stirred at room temperature for 15 h. The reaction mixture was concentrated in vacuo and the residue obtained was purified by flash chromatography [silica-gel using initially ethyl acetate-hexane (1:2) and then ethyl acetate-hexane (2:1)] to give the titled product as white solid (0.16 g).

¹H-NMR(CDCl₃): δ 8.52 (m, 1H), 8.15 (d,1H), 7.79 (m, 3H), 7.36–7.65 (m,10H), 7.23 (m, 1H), 5.52 (s, 2H), 3.75 (t, 4H), 3.60(s, 2H), 3.51 (s, 1H), 2.52 (t, 4H), 0.91 (s, 9H). FAB-MS: (m/e) 609 (M+H).

Step 2: 4-(Morpholinomethyl)phenyl-2-[(2'-(6-(N-t-butyloxy carbonylamino)hexanoyl)aminosulfonyl)-biphen-4-yl]methyl-phthalazin-1-(2H)-one.

4-(Morpholinomethyl)phenyl-2-[(2'-aminosulfonyl)-biphen-4-yl]methyl-phthalazin-1-(2H)-one [prepared from 4-(Morpholinomethyl)phenyl-2- [(2'-t-butylaminosulfonyl)biphen-4-yl]methyl-phthalazin-1-(2H)-one according to the procedure described in Example 2; Step 2] (0.1 g, 0.18 mMol) was reacted in THF (3 mL) with the acyl-imidazole [prepared from N-t-Boc-aminohexanoic acid (0.083 g, 0.36 mMol) and N,N-carbonyldiimidazole (0.06 g, 0.36 mMol)] and DBU (0.053 mL), according to the procedure described in Example 10. The titled compound was obtained as a foam (0.12 g), after purification of the crude product by flash chromatography (silica-gel, chloroform-methanol-NH₄OH-100:10:1).

¹H-NMR (CDCl₃): δ 8.50 (m, 1H), 8.22 (d,1H), 7.78 (m, 3H), 7.15–7.60 (m,11H), 5.52 (s, 2H), 3.75 (t, 4H), 3.60(s, 2H), 3.0 (m, 2H), 2.52 (t, 4H), 1.84 (t, 2H), 1.44 (s, 9H), 1.1–1.4 (m, 6H). FAB-MS: (m/e) 780 (M+H).

Step 3: 4-(Morpholinomethyl)phenyl-2-[(2'-(6-aminohexanoyl)-aminosulfonyl)-biphen-4-yl] methyl-phthalazin-1-(2H)-one.

4-(Morpholinomethyl)phenyl-2- [(2'-(6-(N-t-butyloxy-carbonylamino)hexanoyl)aminosulfonyl)-biphen-4-yl]- methyl-phthalazin-1-(2H)-one, obtained in step 2, (0.10 g) was dissolved in a mixture of methylene chloride (1 mL) and anhydrous trifluoroacetic acid (1 mL). The mixture was stirred at room temperature for 1 h then concentrated in vacuo to dryness. Dry ether was added and the solid obtained was filtered and dried to give the titled compound as the ditrifluoroacetic acid salt (0.08 g).

$^1$H-NMR (CD$_3$OD): δ 8.50 (m, 1H), 8.22 (d,1H), 7.78 (m, 3H), 7.15–7.60 (m,11H), 5.52 (s, 2H), 3.75 (t, 4H), 3.60(s, 2H), 3.0 (m, 2H), 2.52 (t, 4H), 1.84 (t, 2H), 1.2–1.4 (m, 6H). FAB-MS: (m/e) 680 (M+H)

EXAMPLE 49

Typical Pharmaceutical Compositions Containing a Compound of the Invention [e.g. 4-p-toluyl-2-(2'-(5-(N,N-dimethyl-carboxamido)-pentanoyl) aminosulfonyl)biphen-4-yl)methyl-phthalazin-1-(2H)-one (Example 26)].

A: Dry Filled Capsules Containing 50 mg of Active Ingredient Per Capsule

| Ingredient | Amount per capsule (mg) |
| --- | --- |
| Title compound of Example 26 | 50 |
| Lactose | 149 |
| Magnesium stearate | 1 |
| Capsule (size No. 1) | 200 |

The title compound of Example 26 can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain the title compound of Example 26 (25 mg), pregelatinized starch USP (82 mg), microcrystalline cellulose (82 mg)and magnesium stearate (1 mg).

C: Suppository

Typical suppository formulations for rectal administration can contain the title compound of Example 26 (1–25 mg), butylated hydroxyanisole (0.08–1.0 mg), disodium calcium acetate (0.25–0.5 mg), and polyethylene glycol (775–1600 mg). Other suppository formulations can be made by substituting, for example, butylated hydroxytoluene (0.04–0.08 mg) for the disodium calcium acetate and a hydrogenated vegetable oil (675–1400 mg) such as Suppocire L, Wecobee FS, Wecobee M, Witepsols, and the like, for the polyethylene glycol.

D: Injection

A typical injectable formulation would contain the title compound of Example 26 (5.42 mg), sodium phosphate dibasic anhydrous (11.4 mg) benzyl alcohol (0.01 ml) and water for injection (1.0 ml).

What is claimed is:
1. A compound of structural formula I:

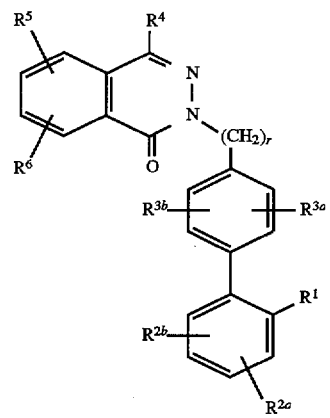

or a pharmaceutically acceptable salt thereof, wherein:
$R^1$ is:
- (a) —NHSO$_2$NHCOR$^9$,
- (b) —NHCONHSO$_2$R$^9$,
- (c) —SO$_2$NHR$^9$,
- (d) —SO$_2$NHCOR$^9$,
- (e) —SO$_2$NHCONR$^7$R$^9$, or
- (f) —SO$_2$NHCOOR$^9$;

$R^{2a}$ and $R^{2b}$ are each independently:
- (a) H,
- (b) Cl, Br, I, F,
- (c) CF$_3$,
- (d) C$_1$–C$_6$-alkyl,
- (e) C$_1$–C$_6$-alkoxy,
- (f) C$_1$–C$_6$-alkyl-S—,
- (g) C$_2$–C$_6$-alkenyl,
- (h) C$_2$–C$_6$-alkynyl,
- (i) C$_3$–C$_7$-cycloalkyl,
- (j) aryl, where aryl is as defined in R$^4$ (c) below, or
- (k) aryl-C$_1$–C$_6$-alkyl, where aryl is as defined in R$^4$ (c) below;

$R^{3a}$ is:
- (a) H,
- (b) Cl, Br, I, F,
- (c) C$_1$–C$_6$-alkyl,
- (d) C$_1$–C$_6$-alkoxy, or
- (e) C$_1$–C$_6$-alkoxyalkyl;

$R^{3b}$ is:
- (a) H,
- (b) Cl, Br, I, F,
- (c) C$_1$–C$_6$-alkyl,
- (d) C$_3$–C$_7$-cycloalkyl,
- (e) C$_1$–C$_6$-alkoxy,
- (f) CF$_3$,
- (g) C$_2$–C$_6$-alkenyl, or
- (h) C$_2$–C$_6$-alkynyl;

$R^4$ is:
- (a) H,
- (b) (C$_1$–C$_6$)-alkyl, optionally substituted with a substituent selected from the group consisting of: C$_1$–C$_4$-alkoxy, aryl, where aryl is as defined in R$^4$ (c) below, heteroaryl, where heteroaryl is as defined below, —CON(R$^{10}$)$_2$, —N(R$^{10}$)$_2$, —O—COR$^{10}$ and —COR$^{10}$ or
- (c) aryl, wherein aryl is phenyl or naphthyl, either unsubstituted or substituted with one or two substituents selected from the group consisting of Cl, F, Br, I, $N(R^7)_2$, $NR^7COOR^9$, $NR^7CONR^7R^9$, $CO_2R^7$, $CONR^7R^9$, $C_1$–$C_4$-alkyl, —($C_1$–$C_4$)alkyl-Y, $NO_2$, OH, $CF_3$, $C_1$–$C_4$-alkoxy, —$S(O)_x$—($C_1$–$C_4$)alkyl, and —($C_1$–$C_4$)alkyl-N-($CH_2$—$CH_2$)$_2$Q, (d) heteroaryl, wherein heteroaryl is defined as pyridyl, and wherein the heteroaryl is unsubstituted or substituted with one or two substituents selected from the group consisting of: —OH, —SH, —$C_1$–$C_4$-alkyl, —$C_1$–$C_4$-alkoxy, —$CF_3$, Cl, Br, F, I, —$NO_2$, —$CO_2H$, —$CO_2$—($C_1$–$C_4$-alkyl), —$NH_2$, —NH ($C_1$–$C_4$-alkyl) and —N($C_1$–$C_4$-alkyl)$_2$, $NR^7COOR^9$ and $NR^7CONR^7R^9$, (e) $C_3$–$C_7$-cycloalkyl, or (f) —COaryl, where aryl is as defined in $R^4$ (c) above;

Q is:
a single bond, —$CH_2$—, O, $NR^7$, or $S(O)_x$;

Y is:
$COOR^9$, CN, $NR^7COOR^9$ or $CONR^7R^9$;

$R^5$ and $R^6$ are independently:
(a) H,
(b) $C_1$–$C_6$-alkyl, unsubstituted or substituted with a substituent selected from the group consisting of: —OH, -guanidino, $C_1$–$C_4$-alkoxy, —$N(R^7)_2$, $COOR^7$, —$CON(R^7)_2$, —O—$COR^7$, -aryl, where aryl is as defined in $R^4$ (c) above, -heteroaryl, where heteroaryl is as defined in $R^4$ (d) above, —$S(O)_x$—$R^9$, -tetrazol-5-yl, —$CONHSO_2R^9$,—$SO_2NH$-heteroaryl, where heteroaryl is as defined in $R^4$ (d) above, —$SO_2NHCOR^9$, —$PO(OR^7)_2$, —$PO(OR^8)R^7$, —$SO_2NH$—CN, —$NR^8COOR^9$, morpholino, N-($C_1$–$C_6$-alkyl)-piperazinyl, and —$COR^7$,
(c) —CO-aryl, where aryl is as defined in $R^4$(c) above,
(d) —$C_3$–$C_7$-cycloalkyl,
(e) Cl, Br, I, F,
(f) —OH,
(g) —$OR^9$,
(h) —$C_1$–$C_4$-Perfluoroalkyl,
(i) —$S(O)_x$—$R^9$,
(j) —$COOR^7$,
(k) —$SO_3H$,
(l) —$NR^7R^9$,
(m) —$NR^7COR^9$,
(n) —$NR^7COOR^9$,
(o) —$SO_2NR^7R^8$,
(p) —$NO_2$,
(q) —$NR^7SO_2R^9$,
(r) —$NR^7CONR^7R^9$,
(s) —$OCONR^9R^7$,
(t) -aryl, where aryl is as defined in $R^4$(c) above,
(u) —$NHSO_2CF_3$,
(v) —$SO_2NH$-heteroaryl, where heteroaryl is as defined in $R^4$(d) above,
(w) —$SO_2NHCOR^9$,
(x) —$CONHSO_2R^9$,
(y) —$PO(OR^7)_2$,
(z) —$PO(OR^8)R^7$,
(aa) -tetrazol-5-yl,
(bb) —CONH(tetrazol -5-yl),
(cc) —$COR^7$,
(dd) —$SO_2NHCN$,
(ee) —CO-heteroaryl, where heteroaryl is as defined in R4(d) above,
(ff) —$NR^7SO_2NR^9R^7$,
(gg) —$N[CH_2CH_2]_2NR^{11}$,
(hh) —$N[CH_2CH_2]_2O$, or
(ii) -heteroaryl, where heteroaryl is as defined in R4(d) above;

x is:
0, 1, or 2, $R^7$ is:
H, $C_1$–$C_5$-alkyl, aryl, or —$CH_2$-aryl, where aryl is as defined in $R^4$(c) above;

$R^8$ is:
H, or $C_1$–$C_4$-alkyl;

$R^9$ is:
(a) aryl, where aryl is as defined in $R^4$(c) above,
(b) heteroaryl, where heteroaryl is as defined in $R^4$(d) above,
(c) $C_3$–$C_7$-cycloalkyl,
(d) $C_1$–$C_8$-alkyl, wherein alkyl is unsubstituted or substituted with one or two substituents selected from the group consisting of: aryl, where aryl is as defined in $R^4$(c) above, heteroaryl, where heteroaryl is as defined in $R^4$(d) above, —OH, —SH, $C_1$–$C_4$-alkyl, —O($C_1$–$C_4$-alkyl), —S ($C_1$–$C_4$-alkyl), —$CF_3$, Cl, Br, F, I, —$NO_2$, —$CO_2H$, —$CO_2$—$C_1$–$C_4$-alkyl, —$NH_2$, —$NR^7CO_2R^{10}$, —$NH(C_1$–$C_4$-alkyl), —$N(C_1$–$C_4$-alkyl)$_2$, —$PO_3H_2$, —$PO(OH)(O$—$C_1$–$C_4$-alkyl), —$PO(OR^8)R^7$, —$NR^7COR^{10}$, —$CONR^7R^{10}$, —$OCONR^7R^{10}$, —$SO_2NR^7R^{10}$, —$NR^7SO_2R^{10}$, —$N(CH_2$—$CH_2)_2Q$ and —CON($CH_2$—$CH_2$)$_2$Q or
(e) perfluoro-$C_1$–$C_4$-alkyl;

$R^{10}$ is:
(a) aryl, where aryl is as defined in $R^4$(c) above,
(b) heteroaryl, where heteroaryl is as defined in $R^4$(d) above,
(c) $C_1$–$C_6$-alkyl, wherein alkyl is unsubstituted or substituted with a substituent selected from the group consisting of: aryl, where aryl is as defined in $R^4$(c) above, heteroaryl, where heteroaryl is as defined in $R^4$(d) above, —OH, —$NH_2$, —$NH(C_1$–$C_4$-alkyl), —$N(C_1$–$C_4$-alkyl)$_2$, —$CO_2R^7$, Cl, Br, F, I, and —$CF_3$, or
(d) perfluoro-$C_1$–$C_4$-alkyl;

$R^{11}$ is:
$C_1$–$C_6$-alkyl, $C_3$–$C_7$-cycloalkyl, —$CONR^7R^8$, heteroaryl, where heteroaryl is as defined in $R^4$(d) above, phenyl, —CO—$C_3$–$C_7$-cycloalkyl, or —CO—$C_1$–$C_6$-alkyl; and r is:
1 or 2.

2. The compound of claim 1, wherein:
$R^1$ is:
(a) —$NHSO_2NHCOR^9$, or
(b) —$NHCONHSO_2R^9$;

$R^{2a}$ is:
H;

$R^{2b}$ is:
H, F, Cl, $CF_3$, $C_1$–$C_6$-alkyl, $C_2$–$C_4$-alkenyl, or $C_2$–$C_4$-alkynyl, aryl, wherein aryl is phenyl or naphthyl, either unsubstituted or substituted with one or two substituents selected from the group consisting of Cl, F, Br, I, $N(R^7)_2$, $NR^7COOR^9$, $NR^7CONR^7R^9$, $CO_2R^7$, $CONR^7R^9$, $C_1$–$C_4$-alkyl, -($C_1$–$C_4$)alkyl-Y, $NO_2$, OH, $CF_3$, $C_1$–$C_4$-alkoxy, —$S(O)_x$—($C_1$–$C_4$) alkyl, and —($C_1$–$C_4$)alkyl-N-($CH_2$—$CH_2$)$_2$Q, or aryl-$C_1$–$C_6$ alkyl, where aryl is as defined above;

$R^{3a}$ is:
H;

$R^{3b}$ is:
H, F, Cl, $CF_3$, $C_1$–$C_4$-alkyl, $C_2$–$C_4$-alkenyl, $C_2$–$C_4$-alkynyl, or $C_5$–$C_6$-cycloalkyl;

$R^5$ and $R^6$ are each independently:
 (a) H,
 (b) $C_1$–$C_6$-alkyl unsubstimted or substituted with $COOR^7$, $OCOR^7$, OH, or aryl, where aryl is as defined in $R^{2b}$ above,
 (c) —OH,
 (d) —$NO_2$,
 (e) —$NHCOR^9$,
 (f) —$C_1$–$C_4$-alkoxy,
 (g) —$NHCO_2R^9$,
 (h) —$NR^7R^9$,
 (i) —Cl, F, Br,
 (j) —$CF_3$,
 (k) —$CO_2R^7$,
 (l) —CO-aryl, where aryl is as defined in $R^{2b}$ above,
 (m) —$S(O)_x$—$C_1$–$C_4$-alkyl,
 (n) —$S_{O2}$—NH—$C_1$–$C_4$-alkyl,
 (o) —$SO_2$—NH-aryl, where aryl is as defined in $R^{2b}$ above,
 (P) —$NHSO_2CH_3$,
 (q) -aryl, where aryl is as defined in $R^{2b}$ above,
 (r) —$NHCONR^7R^9$,
 (s) —$N[CH_2CH_2]_2NR^{11}$, or
 (t) —$N[CH_2CH]_2O$;
r is
 one.

3. The compound of claim 2, wherein:
$R^1$ is:
 (a) —$NHSO_2NHCOR^9$, or
 (b) —$NHCONHSO_2R^9$;
$R^4$ is:
 H, $(C_1$–$C_6)$-alkyl, aryl, wherein aryl is phenyl or naphthyl, either unsubstimted or substituted with one or two substituents selected from the group consisting of Cl, F, Br, I, $N(R^7)_2$, $NR^7COOR^9$, $NR^7CONR^7R^9$, $CO_2R^7$, $CONR^7R^9$, $C_1$–$C_4$-alkyl, —$(C_1$–$C_4)$alkyl-Y, $NO_2$, OH, $CF_3$, $C_1$–$C_4$-alkoxy, —$S(O)_x$—$(C_1$–$C_4)$alkyl, and-$(C_1$–$C_4)$alkyl-N-$(CH_2$—$CH_2)_2$Q, or aryl-$(C_1$–$C_6)$-alkyl, where aryl is as defined above, or heteroaryl, wherein heteroaryl is defined as pyridyl and wherein the heteroaryl is unsubstimted or substituted with one or two substituents selected from the group consisting of: —OH, —SH, —$C_1$–$C_4$-alkyl, —$C_1$–$C_4$-alkoxy, —$CF_3$, Cl, Br, F, I, —$NO_2$, —$CO_2H$, —$CO_2$—$(C_1$–$C_4$-alkyl), —$NH_2$, —$NH(C_1$–$C_4$-alcyl) and —$N(C_1$–$C_4$-alkyl)$_2$, $NR^7COOR^9$ and $NR^7CONR^7R^9$; and
$R^5$ and $R^6$ are each independently:
 H, —$C_1$–$C_4$-alkyl, -aryl, where aryl is as defined in $R^4$ above, —$NO_2$, —$NR^7R^9$, —$NHCOOR^9$, —Cl, $CH_2COOH$, —$S(O)_x$—$C_1$–$C_4$-alkyl, $NHCONR^7R^9$, $NHCOR^9$, $CO_2R^9$, —F, $N[CH_2CH_2]_2NR^{11}$, or $N[CH_2CH_2]_2O$.

4. The compound of claim 1, wherein:
$R^1$ is:
 (a) —$SO_2NHR^9$,
 (b) —$SO_2NHCOR^9$,
 (c) —$SO_2NHCONR^7R^9$, or
 (d) —$SO_2NHCOOR^9$;
$R^{2a}$ is:
 H;
$R^{2b}$ is:
 H, F, Cl, $CF_3$, $C_1$–$C_6$-alkyl, $C_2$–$C_4$-alkenyl, or $C_2$–$C_4$-alkynyl, aryl, wherein aryl is phenyl or naphthyl, either unsubstituted or substituted with one or two substituents selected from the group consisting of Cl, F, Br, I, $N(R^7)_2$, $NR^7COOR^9$, $NR^7CONR^7R^9$, $CO_2R^7$, $CONR^7R^9$, $C_1$–$C_4$-alkyl, —$(C_1$–$C_4)$alkyl-Y, $NO_2$, OH, $CF_3$, $C_1$–$C_4$-alkoxy, —$S(O)_x$—$(C_1$–$C_4)$alkyl, and —$(C_1$–$C_4)$alkyl-N-$(CH_2$—$CH_2)_2$Q, or aryl-$C_1$–$C_6$-alkyl, where aryl is as defined above;
$R^{3a}$ is:
 H;
$R^3$ is:
 H, F, Cl, $CF_3$, $C_1$–$C_4$-alkyl, $C_2$–$C_4$-alkenyl, $C_2$–$C_4$-alkynyl, or $C_5$–$C_6$-cycloalkyl;
$R^5$ and $R^6$ are independently:
 (a) H,
 (b) $C_1$–$C_6$-alkyl, unsubstituted or substituted with $COOR^7$, $OCOR^7$, OH, or aryl, where aryl is as defined in $R^{2b}$ above,
 (c) —OH,
 (d) —$NO_2$,
 (e) —$NHCOR^9$,
 (f) —$C_1$–$C_4$-alkoxy,
 (g) —$NHCO_2R^9$,
 (h) —$NR^7R^9$,
 (i) —Cl, F, Br,
 (j) —$CF_3$,
 (k) —$CO_2R^7$,
 (l) —CO-aryl, where aryl is as defined in $R^{2b}$ above,
 (m) —$S(O)_x$—$C_1$–$C_4$-alkyl,
 (n) —$SO_2$—NH—$C_1$–$C_4$-alkyl,
 (o) —$SO_2$—NH-aryl, where aryl is as defined in $R^{2b}$ above,
 (P) —$NHSO_2CH_3$,
 (q) -aryl, where aryl is as defined in $R^{2b}$ above,
 (r) —$NHCONR^7R^9$,
 (s) —$N[CH_2CH_2]_2NR^{11}$, or
 (t) —$N[CH_2CH_2]_2O$; and
r is
 one.

5. The compound of claim 4, wherein:
$R^1$ is:
 (a) —$SO_2NHR^9$,
 (b) —$SO_2NHCOR^9$,
 (c) —$SO_2NHCONR^7R^9$, or
 (d) —$SO_2NHCOOR^9$;
$R^4$ is:
 H, $(C_1$–$C_6)$-alkyl, aryl, wherein aryl is phenyl or naphthyl, either unsubstimted or substituted with one or two substituents selected from the group consisting of Cl, F, Br, I, $N(R^7)_2$, $NR^7COOR^9$, $NR^7CONR^7R^9$, $CO_2R^7$, $CONR^7R^9$, $C_1$–$C_4$-alkyl, —$(C_1$–$C_4)$alkyl-Y, $NO_2$, OH, $CF_3$, $C_1$–$C_4$-alkoxy, —$S(O)_x$—$(C_1$–$C_4)$alkyl, and —$(C_1$–$C_4)$alkyl-N—$(CH_2$—$CH_2)_2$Q, or aryl-$(C_1$–$C_6)$-alkyl, where aryl is as defined above, or heteroaryl, wherein heteroaryl is defined as pyridyl and wherein the heteroaryl is unsubstimted or substituted with one or two substituents selected from the group consisting of: —OH, —SH, —$C_1$–$C_4$-alkyl, —$C_1$–$C_4$-alkoxy, —$CF_3$, Cl, Br, F, I, —$NO_2$, —$CO_2H$, —$CO_2$—$(C_1$–$C_4$-alkyl), —$NH_2$, —$NH(C_1$–$C_4$-alkyl) and —$N(C_1$–$C_4$-alkyl)$_2$, $NR^7COOR^9$ and $NR^7CONR^7R^9$; and
$R^5$ and $R^6$ are each independently:
 H, —$C_1$–$C_4$-alkyl, -aryl, where aryl is as defined in $R^4$ above, —$NO_2$, —$NR^7R^9$, —$NHCOOR^9$, —Cl, —$CH_2COOH$, —$S(O)_x$—$C_1$–$C_4$-alkyl, $NHCONR^7R^9$, $NHCOR^9$, $CO_2R^7$, —F, $N[CH_2CH_2]_2NR^{11}$, or $N[CH_2CH_2]_2O$.

6. A compound of structural formula

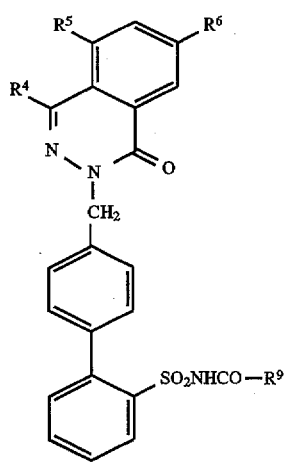

wherein the substituents are as defined in Table 1 below and Boc is defined as N-tert-butoxycarbonyl and Ac is defined as acetyl:

TABLE I

| $R^4$ | $R^5$ | $R^6$ | $R^9$ |
|---|---|---|---|
| H | H | H | —$(CH_2)_5$NHBoc |
| H | H | H | —$(CH_2)_5NH_2$ |
| Methyl | H | H | —$(CH_2)_5$NHBoc |
| Methyl | H | H | —$(CH_2)_5NH_2$ |
| n-Propyl | H | i-propyl | —$(CH_2)_5$NHBoc |
| n-Propyl | H | H | —$(CH_2)_5$NHBoc |
| n-Propyl | H | H | —$(CH_2)_5NH_2$ |
| i-Propyl | H | H | -cyclopropyl |
| i-Propyl | H | H | —$(CH_2)_4$NHBoc |
| i-Propyl | H | H | —$(CH_2)_4NH_2$ |
| Phenyl | H | H | -cyclopropyl |
| Phenyl | H | H | —$(CH_2)_5$NHBoc |
| Phenyl | H | H | —$(CH_2)_5NH_2$ |
| Phenyl | methyl | H | —$(CH_2)_5$NHBoc |
| Phenyl | methyl | H | —$(CH_2)_5NH_2$ |
| p-Toluyl | H | H | —$(CH_2)_5$NHCOCH$_3$ |
| p-Toluyl | H | methyl | —$(CH_2)_5NH_2$ |
| p-Toluyl | H | methyl | —$(CH_2)_5$NHBoc |
| 4-Cl-Phenyl | H | H | —$(CH_2)_5$NHBoc |
| 4-Cl-Phenyl | H | H | —$(CH_2)_5NH_2$ |
| 4-Cl-Phenyl | H | H | —$(CH_2)_4$CON(CH$_3$)$_2$ |
| 4-Cl-Phenyl | H | methyl | —$(CH_2)_5$NHBoc |
| 4-Br-Phenyl | H | H | —$(CH_2)_5$NHBoc |
| 4-Br-Phenyl | H | H | —$(CH_2)_5NH_2$ |
| 4-F-Phenyl | H | H | —$(CH_2)_5$NHBoc |
| 4-F-Phenyl | H | H | —$(CH_2)_5NH_2$ |
| 4-OMe-Phenyl | H | H | —$(CH_2)_5$NHBoc |
| 4-OMe-Phenyl | H | H | —$(CH_2)_5NH_2$ |
| p-Toluyl | H | H | —$(CH_2)_5$NHBoc |
| p-Toluyl | H | H | —$(CH_2)_5NH_2$ |
| p-Toluyl | H | H | —$(CH_2)_6$NHBoc |
| p-Toluyl | H | H | —$(CH_2)_6NH_2$ |
| p-Toluyl | H | H | —$(CH_2)_3$NHBoc |
| p-Toluyl | H | H | —$(CH_2)_3NH_2$ |
| p-Toluyl | H | H | —$(CH_2)_4$NHBoc |
| P-Toluyl | B | H | —$(CH_2)_4NH_2$ |
| p-Toluyl | H | H | —$(CH_2)_6$OH |
| p-Toluyl | H | H | —$(CH_2)_5$COOC$_2$H$_5$ |
| p-Toluyl | H | H | —$(CH_2)_4$COOH |
| p-Toluyl | methyl | H | —$(CH_2)_5$COOC$_2$H$_5$ |
| p-Toluyl | H | H | —$(CH_2)_6$CH$_3$ |
| p-Toluyl | H | H | —$(CH_2)_5$CONHCH$_3$ |
| p-Toluyl | H | H | —$(CH_2)_5$CON(CH$_3$)$_2$ |
| p-Toluyl | H | H | —$(CH_2)_4$CON(CH$_3$)$_2$ |
| p-Toluyl | H | H | —$(CH_2)_4$CON(CH$_2$)$_4$ |
| p-Toluyl | H | H | —$(CH_2)_4$CON(CH$_2$)$_5$ |

TABLE I-continued

| $R^4$ | $R^5$ | $R^6$ | $R^9$ |
|---|---|---|---|
| p-Toluyl | H | H | —$(CH_2)_4$CON(CH$_2$CH$_2$)$_2$O |
| p-Toluyl | H | H | —$(CH_2)_4$CON(CH$_2$CH$_2$)$_2$NH |
| p-Toluyl | H | H | —$(CH_2)_4$CON(CH$_2$CH$_2$)$_2$NAc |
| p-Toluyl | H | H | —$(CH_2)_4$CON(CH$_2$CH$_2$)$_2$NCH$_3$ |
| p-Toluyl | H | H | —$(CH_2)_6$CON(CH$_3$)$_2$ |
| p-Toluyl | H | H | —$(CH_2)_2$CH(NHBoc)COOtBu |
| p-Toluyl | H | H | -2-thienyl |
| p-Toluyl | H | H | -3-furyl |
| p-Toluyl | H | H | -2-furyl |
| p-Toluyl | H | H | —$(CH_2)_2$OCH$_3$ |
| p-Toluyl | H | H | —NH(CH$_2$)$_3$CH$_3$ |
| p-Toluyl | H | H | —NH(CH$_2$)$_5$CH$_3$ |
| p-Toluyl | H | H | —NH(CH$_2$)$_3$Cl |
| p-Toluyl | H | H | —NH(CH$_2$)$_2$-2-thienyl |
| p-Toluyl | H | H | —CH$_2$OCH$_2$CH$_3$ |
| p-Toluyl | H | H | —$(CH_2)_5$OH |
| p-Toluyl | H | H | —NH(CH$_2$)$_5$CH$_3$ |
| p-Toluyl | H | H | —$(CH_2)_5$N(CH$_3$)$_2$ |
| p-Toluyl | H | H | —$(CH_2)_5$NHCH$_3$ |
| p-Toluyl | H | H | —$(CH_2)_5$N(CH$_3$)$_2$ |
| 1-Naphthyl | H | H | —$(CH_2)_5$CON(CH$_3$)$_2$ |
| 1-Naphthyl | H | H | —$(CH_2)_4$CON(CH$_3$)$_2$ |
| 1-Naphthyl | H | H | —$(CH_2)_5$NHBoc |
| 1-Naphthyl | H | H | —$(CH_2)_5NH_2$ |
| 4-OMe-Phenyl | H | H | —$(CH_2)_5$CON(CH$_3$)$_2$ |
| 4-OMe-Phenyl | H | H | —$(CH_2)_4$CON(CH$_3$)$_2$ |
| 2-Naphthyl | H | H | —$(CH_2)_5$N(CH$_3$)$_2$ |
| 2-Naphthyl | H | H | —$(CH_2)_5$CON(CH$_3$)$_2$ |
| 2-Naphthyl | H | H | —$(CH_2)_4$CON(CH$_3$)$_2$ |
| 2-Naphthyl | H | H | —$(CH_2)_5$NHBoc |
| 2-Naphthyl | H | H | —$(CH_2)_5NH_2$ |
| Pentamethylphenyl | H | H | —$(CH_2)_5NH_2$ |
| Pentamethylphenyl | H | H | —$(CH_2)_5$NHBoc |
| Pentamethylphenyl | H | H | —$(CH_2)_4$CON(CH$_3$)$_2$ |
| 2-pyridyl | H | H | —$(CH_2)_4$CON(CH$_3$)$_2$ |
| 4-pyridyl | H | H | —$(CH_2)_4$CON(CH$_3$)$_2$ |
| 2-Thienyl | H | H | —$(CH_2)_4$CON(CH$_3$)$_2$ |
| 2-pyridyl | H | H | —$(CH_2)_5$NHBoc |
| 2-pyridyl | H | H | —$(CH_2)_5NH_2$ |
| 2-pyridyl | H | H | —$(CH_2)_5$N(CH$_3$)$_2$ |
| 4-pyridyl | H | H | —$(CH_2)_5$NHBoc |
| 4-pyridyl | H | H | —$(CH_2)_5NH_2$ |
| 4-pyridyl | H | H | —$(CH_2)_5$N(CH$_3$)$_2$ |
| 4-pyridyl | H | H | —$(CH_2)_4$CON(CH$_3$)$_2$ |
| 2-Thienyl | H | H | —$(CH_2)_4$CON(CH$_3$)$_2$ |
| 4-(N-Morpholino-methyl)phenyl | H | H | —$(CH_2)_5$NHBoc |
| 4-(N-Morpholino-methyl)phenyl | H | H | —$(CH_2)_5NH_2$ |
| 4-(N-Pyrrolidino-methyl)phenyl | H | H | —$(CH_2)_5$NHBoc |
| 4-(N-Pyrrolidino-methyl)phenyl | H | H | —$(CH_2)_5NH_2$ |
| 4-(N-Pyrrolidino-methyl)phenyl | H | H | —$(CH_2)_4$CON(CH$_3$)$_2$ |
| 4-(N-Morpholino-methyl)phenyl | H | H | —$(CH_2)_4$CON(CH$_3$)$_2$ |
| p-Toluyl | H | H | —$(CH_2)_3$CON(CH$_3$)$_2$ |
| p-Toluyl | H | H | —$(CH_2)_5$NHCON(CH$_3$)$_2$ |
| p-Toluyl | H | H | —$(CH_2)_5$NHSO$_2$iPr |
| p-Toluyl | H | H | —$(CH_2)_3$NHCON(CH$_3$)$_2$ |
| p-Toluyl | H | H | —NH(CH$_2$)$_3$CON(CH$_3$)$_2$ |
| p-Toluyl | H | H | —$(CH_2)_3$NHCOCH$_3$ |
| p-Toluyl | H | H | —$(CH_2)_4$CONH$_2$ |
| p-Toluyl | H | H | —$(CH_2)_4$CONHCH$_3$ |
| 4-Cl-Phenyl | H | H | —$(CH_2)_4$CON(CH$_3$)$_2$ |
| 4-F-Phenyl | H | H | —$(CH_2)_4$CON(CH$_3$)$_2$ |
| 2-CH$_3$CONH-Phenyl | H | H | —$(CH_2)_4$CON(CH$_3$)$_2$.— |

* * * * *

UNITED STATES PATENT AND TRADEMARK OFFICE
CERTIFICATE OF CORRECTION

PATENT NO. : 5,668,279

DATED : September 16, 1997

INVENTOR(S) : Prasun K. Chakravarty, Elizabeth M. Naylor and Anna Chen

Page 1 of 2

It is certified that error appears in the above-identified patent and that said Letters Patent is hereby corrected as shown below:

Column 37, Claim 1, line 6, correct the spelling of "unsubstimted" to read -- unsubstituted --.

Column 39, Claim 2, line 3, correct the spelling of "unsubstimted" to read -- unsubstituted --.

Column 39, Claim 2, line 11, should read -- (g) -$NHCO_2R^9$, --.

Column 39, Claim 2, line 18, should read -- (n) -$SO_2$-NH-$C_1$-$C_4$-alkyl, --.

Column 39, Claim 3, line 34, correct the spelling of "unsubstimted" to read -- unsubstituted --.

Column 39, Claim 3, line 43, correct the spelling of "unsubstimted" to read -- unsubstituted --.

Column 39, Claim 3, line 47, correct the spelling of "-NH($C_1$-$C_4$-alcyl)" to read -- -NH($C_1$-$C_4$alkyl)--.

Column 40, Claim 5, line 47, correct the spelling of "unsubstimted" to read -- unsubstituted --.

Column 40, Claim 5, line 56, correct the spelling of "unsubstimted" to read -- unsubstituted --.

UNITED STATES PATENT AND TRADEMARK OFFICE
CERTIFICATE OF CORRECTION

PATENT NO. : 5,668,279
DATED : September 16, 1997
INVENTOR(S) : Prasun K. Chakravarty, Elizabeth M. Naylor and Anna Chen It is certified that error appears in the above-identified patent and that said Letters Patent is hereby corrected as shown below:

Column 41, Claim 6, line 57, second column of $R^5$ of Table 1, correct the letter "B" to read -- H --.

Signed and Sealed this

Seventeenth Day of February, 1998

Attest:

BRUCE LEHMAN

*Attesting Officer*            *Commissioner of Patents and Trademarks*